US010782295B2

(12) United States Patent
Cravatt et al.

(10) Patent No.: US 10,782,295 B2
(45) Date of Patent: Sep. 22, 2020

(54) CYSTEINE-REACTIVE LIGAND DISCOVERY IN PROTEOMES

(71) Applicant: THE SCRIPPS RESEARCH INSTITUTE, La Jolla, CA (US)

(72) Inventors: Benjamin Cravatt, La Jolla, CA (US); Chu Wang, Beijing (CN); Keriann Backus, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 126 days.

(21) Appl. No.: 14/911,316

(22) PCT Filed: Aug. 13, 2014

(86) PCT No.: PCT/US2014/050828
§ 371 (c)(1),
(2) Date: Feb. 10, 2016

(87) PCT Pub. No.: WO2015/023724
PCT Pub. Date: Feb. 19, 2015

(65) Prior Publication Data

US 2016/0252509 A1 Sep. 1, 2016

Related U.S. Application Data

(60) Provisional application No. 61/865,165, filed on Aug. 13, 2013.

(51) Int. Cl.
*G01N 33/573* (2006.01)
*C12N 9/12* (2006.01)
*C40B 30/00* (2006.01)
*G01N 33/68* (2006.01)

(52) U.S. Cl.
CPC ............. *G01N 33/573* (2013.01); *C12N 9/12* (2013.01); *G01N 33/6842* (2013.01); *C12Y 207/11025* (2013.01); *G01N 2333/91205* (2013.01); *G01N 2500/04* (2013.01); *G01N 2500/10* (2013.01)

(58) Field of Classification Search
CPC ................................ G01N 33/573; C12N 9/12
See application file for complete search history.

(56) References Cited

U.S. PATENT DOCUMENTS

| | | | | |
|---|---|---|---|---|
| 4,469,863 | A | 9/1984 | Ts'o et al. | |
| 5,034,506 | A | 7/1991 | Summerton et al. | |
| 5,216,141 | A | 6/1993 | Benner | |
| 5,235,033 | A | 8/1993 | Summerton et al. | |
| 5,386,023 | A | 1/1995 | Sanghvi et al. | |
| 5,602,240 | A | 2/1997 | De et al. | |
| 5,637,684 | A | 6/1997 | Cook et al. | |
| 5,644,048 | A | 7/1997 | Yau | |
| 6,344,330 | B1 | 2/2002 | Ellman et al. | |
| 7,348,437 | B2 | 3/2008 | Cravatt et al. | |
| 8,669,065 | B1 | 3/2014 | Hansen et al. | |
| 8,778,302 | B2 | 7/2014 | Tai et al. | |
| 10,168,342 | B2 | 1/2019 | Cravatt et al. | |
| 2009/0068107 | A1* | 3/2009 | Cravatt ................ | A61K 31/325 424/9.1 |
| 2010/0021950 | A1 | 1/2010 | Lammert et al. | |
| 2010/0179118 | A1 | 7/2010 | Ozawa et al. | |
| 2010/0184661 | A1 | 7/2010 | Luo et al. | |
| 2010/0203647 | A1 | 8/2010 | Hang et al. | |
| 2011/0020837 | A1 | 1/2011 | Haberkant et al. | |
| 2011/0195527 | A1 | 8/2011 | O'Neill et al. | |
| 2012/0225434 | A1 | 9/2012 | Ciufolini et al. | |
| 2013/0165337 | A1 | 6/2013 | Robinson et al. | |
| 2014/0243430 | A1 | 8/2014 | Geho et al. | |
| 2014/0357512 | A1 | 12/2014 | Yang et al. | |
| 2017/0115303 | A1 | 4/2017 | Cravatt et al. | |

FOREIGN PATENT DOCUMENTS

| | | | |
|---|---|---|---|
| WO | WO-0077184 | A1 | 12/2000 |
| WO | WO-0242773 | A2 | 5/2002 |
| WO | WO-2005118833 | A2 | 12/2005 |
| WO | WO-2006112841 | A1 | 10/2006 |
| WO | WO-2009142678 | A1 | 11/2009 |
| WO | WO-2015023724 | A1 | 2/2015 |
| WO | WO-2016029037 | A1 | 2/2016 |
| WO | WO-2017070611 | A1 | 4/2017 |
| WO | WO-2018136555 | A2 | 7/2018 |

OTHER PUBLICATIONS

Deng et al., Proteome-Wide Quantification and Characterization of Oxidation-Sensitive Cysteines in Pathogenic Bacteria, Cell Host & Microbe, 2013, 13, 358-370. (Year: 2013).*
Jacobs et al., Systems Analysis of Protein Modification and Cellular Responses Induced by Electrophile Stress, Accounts of Chemical Research, 2010, 43(5), 673-683. (Year: 2010).*
Long et al., The Metabolic Serine Hydrolases and Their Functions in Mammalian Physiology and Disease, Chemical Reviews, 2011, 111, 6022-6063. (Year: 2011).*

(Continued)

*Primary Examiner* — Amy M Bunker
(74) *Attorney, Agent, or Firm* — Hugh Wang; Thomas Fitting

(57) ABSTRACT

Cells produce electrophilic products with the potential to modify and affect the function of proteins. Chemoproteomic methods have provided a means to qualitatively inventory proteins targeted by endogenous electrophiles; however, ascertaining the potency and specificity of these reactions to identify the most sensitive sites in the proteome to electrophilic modification requires more quantitative methods. Here, we describe a competitive activity-based profiling method for quantifying the reactivity of electrophilic compounds against 1000+ cysteines in parallel in the human proteome. Using this approach, we identify a select set of proteins that constitute hot spots for modification by various lipid-derived electrophiles, including the oxidative stress product 4-hydroxnonenal (HNE). We show that one of these proteins, ZAK kinase, is labeled by HNE on a conserved, active site-proximal cysteine, resulting in enzyme inhibition to create a negative feedback mechanism that can suppress the activation of JNK pathways by oxidative stress.

6 Claims, 14 Drawing Sheets

Specification includes a Sequence Listing.

(56) References Cited

OTHER PUBLICATIONS

Yang et al., ZAK Inhibits Human Lung Cancer Cell Growth Via ERK and JNK Activation in an AP-1-Dependent Manner, Cancer Science, 2010, 101(6), 1374-1381. (Year: 2010).*
Bachoychin et al., The Pharmacological Landscape and Therapeutic Potential of Serine Hydrolases, Nature Reviews, 2012, 11, 52-68. (Year: 2012).*
Weerapana et al., Quantitative Reactivity Profiling Predicts Functional Cysteines in Proteomes, Nature, 2010, 468, 790-797. (Year: 2010).*
Weerapana et al., Supplementary Information, Quantitative Reactivity Profiling Predicts Functional Cysteines in Proteomes, Nature, 2010, 468, 1-263. (Year: 2010).*
Abegg et al. Proteome-Wide Profiling of Targets of Cysteine reactive Small molecules by Using Ethynyl Benziodoxolone Reagents. Angewandte Chemie International Edition 54:10852-10857 (2015).
Ahmad et al. Structure Based Molecular Inhibition of Caspase-8 for Treatment of Multi-Neurodegenerative Disease Using Known Natural Compounds. Bioinformatics 10(4):191-195 (2014).
Aldini et al. Identification of actin as a 15-deoxy-Delta12,14-prostaglandin J2 target in neuroblastoma cells: mass spectrometric, computational, and functional approaches to investigate the effect on cytoskeletal derangement. Biochemistry 46:2707-2718 (2007).
Bachovchin et al. Academic cross-fertilization by public screening yields a remarkable class of protein phosphatase methylesterase-1 inhibitors. PNAS USA 108:6811-6816 (2011).
Ban et al. Tyrosine bioconjugation through aqueous ene-type reactions: a click-like reaction for tyrosine. J Am Chem Soc 132:1523-1525 (2010).
Barelier et al. Discovery of Fragment Molecules That Bind the Human Peroxiredoxin 5 Active Site. PLoS One 5(3):e9744 (2010).
Beaucage, et al. The functionalization of oligonucleotides via phosphoramidite derivative. Tetrahedron. 1993;49(10):1925-63.
Bennaars-Eiden et al. Covalent modification of epithelial fatty acid-binding protein by 4-hydroxynonenal in vitro and in vivo. Evidence for a role in antioxidant biology. J Biol Chem 277:50693-50702 (2002).
Bischoff et al. Amino Acids: Chemistry, Functionality and Selected Non-Enzymatic Post-Translational Modifications. J Proteomics 75:2275-2296 (2012).
Bloem et al. Tissue distribution and functional expression of a cDNA encoding a novel mixed lineage kinase. J Mol Cell Cardiol 33:1739-1750 (2001).
Brill et al. Synthesis of oligodeoxynucleoside phosphorodithioates via thioamidites. J. Am. Chem. Soc. 111:2321-2322 (1989).
Carbone et al. Inhibition of Hsp72-mediated protein refolding by 4-hydroxy-2-nonenal. Chem Res Toxicol 17:1459-1467 (2004).
Carbone et al. Modification of heat shock protein 90 by 4-hydroxynonenal in a rat model of chronic alcoholic liver disease. J Pharmacol Exp Ther 315:8-15 (2005).
Carlsson et al. Screening for genetic mutations. Nature 380(6571):207 (1996).
Chalker et al. Chemical modification of proteins at cysteine: opportunities in chemistry and biology. Chem Asian J 4(5):630-640 (2009).
Chaudhary et al. Probing the phosphoinositide 4,5-bisphosphate binding site of human profilin I. Chemistry & Biology 5(5):273-281 (1998).
Chipuk et al. Sphingolipid metabolism cooperates with BAK and BAX to promote the mitochondrial pathway of apoptosis. Cell 148:988-1000 (2012).
Codreanu et al. Global analysis of protein damage by the lipid electrophile 4-hydroxy-2-nonenal. Mol Cell Proteomics 8:670-680 (2009).
Cohen et al. Structural bioinformatics-based design of selective, irreversible kinase inhibitors. Science 308:1318-1321 (2005).
De Mesmaeker et al. Comparison of Rigid and Flexible Backbones in Antisense Oligonucleotides Bioorg Med Chem Lett 4(3):395-398 (1994).
Dempcy et al. Synthesis of a thymidyl pentamer of deoxyribonucleic guanidine and binding studies with DNA homopolynucleotides PNAS USA 92:6097-6101 (1995).
Derakhshan et al. Unbiased Identification of Cyteine S-Nitrosylation Sites on Proteins. Nat Protocol 2(7):1685-1691 (2007).
Doorn et al. Covalent modification of amino acid nucleophiles by the lipid peroxidation products 4-hydroxy-2-nonenal and 4-oxo-2-nonenal. Chem Res Toxicol 15:1445-1450 (2002).
Dubinina et al. Role of 4-hydroxy-trans-2-nonenal in cell functions. Biochemistry (Most) 75:1069-1087 (2010).
Egholm et al. Peptide nucleic acids (PNA) oligonucleotide analogues with an achiral peptide backbone. J Am Chem Soc 114:1895-1897 (1992).
EP14836595.0 Extended Search Report dated Jun. 6, 2017.
Erlanson et al. Tethering: Fragment-Based Drug Discovery. Annu Rev Biophys Biomol Structure 33:199-223 (2004).
Forman. Reactive oxygen species and alpha,beta-unsaturated aldehydes as second messengers in signal transduction. Ann N Y Acad Sci 1203:35-44 (2010).
Frei et al. Fast and Highly Chemoselective Alkynylation of Thiols with Hypervalent Iodine Reagents Enabled through a Low Energy Barrier Concerted Mechanism. J Am Chem Soc 136:16563-16573 (2014).
Fritz et al. An overview of the chemistry and biology of reactive aldehydes. Free Radic Biol Med 59:85-91 (2012).
Fritz et al. Exploring the biology of lipid peroxidation-derived protein carbonylation. Chem Res Toxicol 24:1411-1419 (2011).
Fujishima et al. Ligand-directed acyl imidazole chemistry for labeling of membrane-bound proteins on live cells. J Am Chem Soc 134:3961-3964 (2012).
Gao et al. Unusual conformation of a 3'-thioformacetal linkage in a DNA duplex. J. Biomolecular NMR.34:17-34 (1994).
Giron et al. Cysteine Tagging for MS-based Proteomics. Mass spectrometry Reviews 30:366-395 (2011).
Gotoh et al. Identification and characterization of a novel MAP kinase kinase kinase, MLTK. J Biol Chem 276:4276-4286 (2001).
Gubbens et al. Photocrosslinking and click chemistry enable the specific detection of proteins interacting with phospholipids at the membrane interface. Chem Biol. 16(1):3-14 (2009).
Gubbens et al. Proteome-wide detection of phospholipid-protein interactions in mitochondria by photocrosslinking and click chemistry. Mol Biosyst 6(10):1751-1759 (2010).
Gueraud et al. Chemistry and biochemistry of lipid peroxidation products. Free Radic Res 44:1098-1124 (2010).
Gushwa et al. Selective targeting of distinct active site nucleophiles by irreversible SRC-family kinase inhibitors. J Am Chem Soc 134:20214-20217 (2012).
Haberkant et al. Protein-lipid interactions: paparazzi hunting for snap-shots. Biol Chem 390:795-803 (2009).
Han et al. A comparative 'bottom up' proteomics strategy for the site-specific identification and quantification of protein modifications by electrophilic lipids. J Proteomics 75:5724-5733 (2012).
Hang et al. Exploring protein lipidation with chemical biology. Chem Rev 111:6341-6358 (2011).
Higdon et al. Methods for imaging and detecting modification of proteins by reactive lipid species. Free Radic Biol Med 47:201-212 (2009.
Horn et al. Oligonucleotides with alternating anionic and cationic phosphoramidate linkages: Synthesis and hybridization of stereo-uniform isomers. Tetrahedron Lett 37:743-746 (1996).
Huang et al. Crystal structure of an inactive Akt2 kinase domain. Structure 11:21-30 (2003).
Hulce et al. Proteome-wide mapping of cholesterol-interacting proteins in mammalian cells. Nat Methods 10(3):259-264 (2013).
Jacob et al. Control of Oxidative Posttranslational Cysteine Modifications: From Intricate Chemistry to Widespread Biological and Medical Applications. Chem Res Toxicol 25:588-604 (2012).
Jacobs et al. Heat shock factor 1 attenuates 4-Hydroxynonenal mediated apoptosis: critical role for heat shock protein 70 induction and stabilization of Bcl-XL. J Biol Chem 282:33412-33420 (2007).
Jenkins et al. The Biosynthesis of Carbocyclic Nucleosides Chem Soc Re 24:169-176 (1995).

(56) References Cited

OTHER PUBLICATIONS

Jung et al. Hybridization of Alternating Cationic/Anionic Oligonucleotides to RNA Segments. Nucleosides & Nucleotides 13(6 &7):1597-1605 (1994).
Kambe et al. Supporting Information—Mapping the Protein Interaction Landscape for Fully Functionalized Small-Molecule Probes in Human Cells. J Am Chem Soc 136(30):10777-10782 (2014).
Keshet et al. Chapter 1: The MAP kinase signaling cascades: a system of hundreds of components regulates a diverse array of physiological functions. Methods Mol Biol 661:3-38 (2010).
Kiedrowshi et al. Parabolic Growth of a Self-Replicating Hexadeoxynucleotide Bearing a 3'-5'-Phosphoamidate Linkage Angew. Chem. Intl. Ed. English 30(4):423-426 (1991).
Kim et al. An azido-biotin reagent for use in the isolation of protein adducts of lipid-derived electrophiles by streptavidin catch and photorelease. Mol Cell Proteomics 8:2080-2089 (2009).
Knight et al. Features of selective kinase inhibitors. Chem Biol 12:621-637 (2005).
Koshkin et al. LNA (locked nucleic acids): An RNA mimic forming exceedingly stable LNA: LNA duplexes. J Am Chem Soc 120:13252-13253 (1998).
Kumagai et al. CERT Mediates Intermembrane Transfer of Various Molecular Species of Ceramides. JBC 280:6488-6495 (2005).
Kutuk et al. Apoptosis signalling by 4-hydroxynonenal: a role for JNK-c-Jun/AP-1 pathway. Redox Rep 12:30-34 (2007).
Leitner et al. Chemistry meets proteomics: the use of chemical tagging reactions for MS-based proteomics. Proteomics 6:5418-5434 (2006).
Leonard et al. Chemical 'omics' approaches for understanding protein cysteine oxidation in biology. Curr Opin Chem Biol 15:88-102 (2011).
Leonarduzzi et al. Signaling kinases modulated by 4-hydroxynonenal. Free Radic Biol Med 37:1694-1702 (2004).
Letsinger et al. Cationic Oligonucleotides J Am Chem Soc 110:4470-4471 (1988).
Letsinger et al. Effects of pendant groups at phosphorus on binding properties of d-ApA analogues. Nucl Acids Res14(8):3487-3499 (1986).
Letsinger et al. Phosphoramidate Analogs of Oligonucleotides J Org Chem 35(11):3800-3803 (1970).
Liu et al. Developing irreversible inhibitors of the protein kinase cysteinome. Chem Biol 20:146-159 (2013).
Lopachin et al. Molecular mechanisms of 4-hydroxy-2-nonenal and acrolein toxicity: nucleophilic targets and adduct formation. Chem Res Toxicol 22:1499-1508 (2009).
Mag et al. Synthesis and selective cleavage of an oligodeoxynucleotide containing a bridged internucleotide 5'-phosphorothioate linkage. Nucleic Acids Res 19(7):1437-1441 (1991).
Marino et al. Proteomics: mapping reactive cysteines. Nat Chem Biol. 7(2):72-73 (2011).
Meier et al. Peptide Nucleic Acids (PNAs)-Unusual Properties of Nonionic Oligonucleotide Analogues. Angew. Chem. Int. Ed. Engl. 31(8):1008-1010 (1992).
Ngo et al. Mutant methionyl-tRNA synthetase from bacteria enables site-selective N-terminal labeling of proteins expressed in mammalian cells. PNAS USA 110:4992-4997 (2013).
Niphakis et al. A Global Map of Lipid-Binding Proteins and Their Ligandability in Cells. Cell 161(7):1668-1680 (2015).
Pace et al. Diverse functional roles of reactive cysteines. ACS Chem Biol 8(2):283-296 (2013).
Parola et al. HNE interacts directly with JNK isoforms in human hepatic stellate cells. J Clin Invest 102:1942-1950 (1998).
Patricelli et al. Functional interrogation of the kinome using nucleotide acyl phosphates. Biochemistry 46:350-358 (2007).
Pauwels et al. Biological activity of new 2-5A analogues. Chemica Scripta 26:141-149 (1986).
PCT/US2014/050828 International Preliminary Report on Patentability dated Feb. 25, 2016.
PCT/US2014/050828 International Search Report and Written Opinion dated Dec. 12, 2014.
PCT/US2016/024148 International Preliminary Report on Patentability dated Oct. 12, 2017.
PCT/US2016/024148 International Search Report and Written Opinion dated Jul. 25, 2016.
PCT/US2016/058308 International Preliminary Report on Patentability dated May 3, 2018.
PCT/US2016/058308 International Search Report and Written Opinion dated Jan. 17, 2017.
PCT/US2018/14104 International Search Report and Written Opinion dated Jul. 26, 2018.
PCT/US2018/14104 Invitation to Pay Additional Fees dated May 31, 2018.
Peng et al. Turning the spotlight on protein-lipid interactions in cells. Curr Opin Chem Biol 21:144-153 (2014).
Perluigi et al. 4-Hydroxy-2-nonenal, a reactive product of lipid peroxidation, and neurodegenerative diseases: a toxic combination illuminated by redox proteomics studies. Antioxid Redox Signal 17:1590-1609 (2012).
Prescher et al. Chemistry in living systems. Nat Chem Biol. 1(1):13-21 (2005).
Rawls, Rebecca L. Optimistic about antisense. Promising clinical results and chemical strategies for further improvements delight antisense drug researchers. C & E News. 35-59 (Jun. 2, 1997).
Roe et al. Proteomic mapping of 4-hydroxynonenal protein modification sites by solid-phase hydrazide chemistry and mass spectrometry. Anal Chem 79:3747-3756 (2007).
Rostovtsev et al. A stepwise huisgen cycloaddition process: copper (i)-catalyzed regioselective "ligation" of azides and terminal alkynes. Angew. Chem. Int. Ed. Engl. 41(14):2596-2599 (2002).
Rudolph et al. Transduction of redox signaling by electrophile-protein reactions. Sci Signal 2:re7 (2009).
Sadaghiani et al. Tagging and detection strategies for activity-based proteomics. Curr Opin Chem Biol. 11(1):20-28 (2007).
Saghatelian et al. Assignment of endogenous substrates to enzymes by global metabolite profiling. Biochemistry 43:14332-14339 (2004).
Sawai et al. Synthesis and Properties of Oligoadenylic Acids Containing 2'-5' Phosphoramide Linkage. Chem. Lett. 13(5):805-808 (1984).
Scotcher et al. Identification of Two Reactive Cysteine Residues in the Tumor Suppressor Protein p53 Using Top-Down FTICR Mass Spectrometry. 22:888-897 (2011).
Shearn et al. Modification of Akt2 by 4-hydroxynonenal inhibits insulin-dependent Akt signaling in HepG2 cells. Biochemistry 50:3984-3996 (2011).
Shen et al. JNK signaling pathway is a key modulator in cell death mediated by reactive oxygen and nitrogen species. Free Radic Biol Med 40:928-939 (2006).
Simon et al. Determining target engagement in living systems. Nat Chem Biol 9(4):200-205 (2013).
Singh et al. The resurgence of covalent drugs. Nat Rev Drug Discov 10(4):307-317 (2011).
Speers et al. Activity-based protein profiling in vivo using a copper(i)-catalyzed azide-alkyne [3+2] cycloaddition. J Am Chem Soc. 125(16):4686-4687 (2003).
Sprinzel et al. Enzymatic incorporation of ATP and CTP analogues into the 3' end of tRNA. Eur J Biochem 81(3):579-589 (1977).
Surh et al. 15-Deoxy-Δ(12,14)-prostaglandin J(2), an electrophilic lipid mediator of anti-inflammatory and pro-resolving signaling. Biochem Pharmacol 82:1335-1351 (2011).
Tate. Recent advances in chemical proteomics: exploring the post-translational proteome. J Chem Biol 1:17-26 (2008).
Uchida. 4-Hydroxy-2-nonenal: a product and mediator of oxidative stress. Prog Lipid Res 42:318-343 (2003).
U.S. Appl. No. 15/080,767 Office Action dated Dec. 19, 2017.
U.S. Appl. No. 15/080,767 Office Action dated May 17, 2017.
U.S. Appl. No. 15/080,767 Office Action dated Oct. 28, 2016.
U.S. Appl. No. 15/331,745 Office Action dated Dec. 29, 2017.
U.S. Appl. No. 15/331,745 Office Action dated Jul. 17, 2017.
U.S. Appl. No. 15/331,745 Office Action dated Jun. 12, 2018.
U.S. Appl. No. 15/331,745 Office Action dated Oct. 9, 2018.
Vila et al. Identification of protein targets of 4-hydroxynonenal using click chemistry for ex vivo biotinylation of azido and alkynyl derivatives. Chem Res Toxicol. 21(2):432-444 (2008).

(56) References Cited

OTHER PUBLICATIONS

Wang et al. A chemoproteomic platform to quantitatively map targets of lipid-derived electrophiles. Nat Methods. 11(1):79-85 (2014).
Wang et al. Complete inhibition of anisomycin and UV radiation but not cytokine induced JNK and p38 activation by an aryl-substituted dihydropyrrolopyrazole quinoline and mixed lineage kinase 7 small interfering RNA. J Biol Chem 280:19298-19305 (2005).
Wang et al. Exploring post-translational arginine modification using chemically synthesized methylglyoxal hydroimidazolones (MG-Hs). J Am Chem Soc 134:8958-8967 (2012).
Washburn et al. Large-scale analysis of the yeast proteome by multidimensional protein identification technology. Nat Biotechnol 19(3):242-247 (2001).
Weerapana et al. Disparate proteome reactivity profiles of carbon electrophiles. Nat Chem Biol 4:405-407 (2008).
Weerapana et al. Quantitative reactivity profiling predicts functional cysteines in proteomes. Nature 468:790-795 (2010).
Wong et al. Small molecule kinase inhibitors block the ZAK-dependent inflammatory effects of doxorubicin. Cancer Biol Ther. 14(1):56-63 (2013).
Xia et al. Photoactivatable lipid probes for studying biomembranes by photoaffinity labeling. Chem Rev. 113(10):7880-7929 (2013).
Yu et al. Effect of C-terminal truncations on MLK7 catalytic activity and JNK activation. Biochem Biophys Res Commun 310:452-457 (2003).
Zhou et al. A structure-guided approach to creating covalent FGFR inhibitors. Chem Biol 17:285-295 (2010).
Deng, Xin et al. Proteome-wide Quantification and Characterization of Oxidation-Sensitive Cysteines in Pathogenic Bacteria. Cell Host Microbe 13, 358-370, Mar. 13, 2013.
Jacobs, Aaron T. et al., Systems Analysis of Protein Modification and Cellular Responses Induced by Electrophile Stress. Accounts of Chemical Research, vol. 43, No. 5, 673-683, May 2010.
Long, Jonathan Z. et al., The Metabolic Serine Hydrolases and Their Functions in Mammalian Physiology and Disease. Chemical Reviews, 111, 6022-6063, 2011.
U.S. Appl. No. 14/911,316 Office Action dated Jan. 12, 2018.
Yang, Jaw-Ji et al., ZAK Inhibits Human Lung Cancer Cell Growth via ERK and JNK Activation in an AP-1-Dependent Manner. Cancer Science, vol. 101, No. 6, 1374-1381, Jun. 2010.

* cited by examiner

LDEs:

4-HYDROXY-2-NONENAL (HNE)

TRANS-2-HEXADECENAL (2-HD)

15-DEOXY-Δ12, 14-PROSTAGLANDIN J2 (15d-PGJ2)

IA-ALKYNE(IA)

CYS LABELED BY IA PROBE

LOSS OF IA PROBE LABELING

MAP3K9

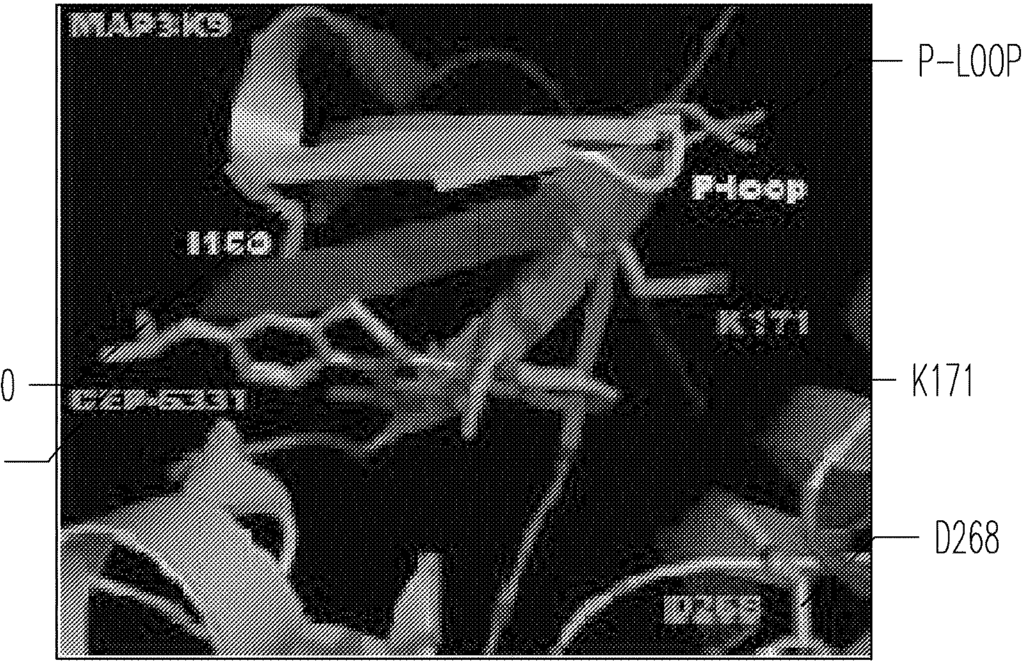

P-LOOP

| | |
|---|---|
| ZAK | LQFFENCGGGSFGSVYR |
| MAP3K1 | WLKGQQIGLGAFSSCYQ |
| MAP3K2 | -RLGKLLGQGAFGRVYL |
| MAP3K3 | WRRGKLLGQGAFGRVYL |
| MAP3K4 | WQRGNKIGEGQYGKVYT |
| MAP3K5 | NGDRVVLGKGTYGIVYA |
| MAP3K6 | TGERLVLGKGTYGVVYA |
| MAP3K7 | IEVEEVVGRGAFGVVCK |
| MAP3K8 | NIGSDFIPRGAFGKVYL |
| MAP3K9 | LTLEEIIGIGGFGKVYR |
| MAP3K10 | LQLEEIIGVGGFGKVYR |
| MAP3K11 | LRLEEVIGIGGFGKVYR |
| MAP3K12 | ILDLQWVGSGAQGAVFL |
| MAP3K13 | ISELQWLGSGAQGAVFL |
| MAP3K14 | ATHQLRLGRGSFGEVHR |
| MAP3K15 | NGERVVLGKGTYGIVYA |
| MAP3K16 | FTDLREIGHGSFGAVYF |
| MAP3K17 | FSDLREIGHGSFGAVYF |
| MAP3K18 | FIGLHEIGHGSFGAVYF |
| MLK4 | LELKELIGAGGFGQVYR |

*Fig. 4A*

CYSTEINE-REACTIVE LIGAND DISCOVERY IN PROTEOMES

CROSS-REFERENCE TO RELATED APPLICATIONS

This application claims the priority of U.S. Ser. No. 61/865,165, filed Aug. 13, 2013, the disclosure of which is incorporated by reference herein in its entirety.

STATEMENT OF GOVERNMENT SUPPORT

This invention was made with government support under grant numbers CA087660 and ES020851 awarded by the National Institutes of Health. The government has certain rights in the invention.

BACKGROUND

The functional diversity of mammalian proteomes is greatly expanded by the post-translational modification (PTM) of proteins[1]. A vast and structurally diverse array of PTMs occurs on proteins to regulate their activity, localization, and interactions with other biomolecules. Many PTMs are enzyme-catalyzed, such as protein phosphorylation, glycosylation, lipidation, and methylation. Our understanding of these enzyme-catalyzed PTMs has benefited greatly from chemoproteomic methods for their global profiling and functional characterization in biological systems[2-4].

Another important class of PTMs includes direct (non-enzymatic) oxidative or electrophilic modification of nucleophilic residues, such as cysteines, in proteins by reactive small molecules that are products of cellular redox reactions[5,6]. When cells, for instance, are subject to various forms of oxidative stress, such as chronic inflammation, hypoxia, or exposure to xenobiotics or environmental pollution, peroxidation of polyunsaturated fatty acids (PUFAs) in the membrane bilayer generates a broad range of secondary products, many of which are electrophilic in nature[5]. These endogenous lipid-derived electrophiles (LDEs) can modify DNA and proteins to promote cytotoxicity and have been implicated in the pathogenesis of many diseases, including cancer, inflammation, neurodegeneration, and cardiovascular disorders. More recently, a growing body of studies has also suggested that, at lower and more physiological concentrations, LDEs can serve as messengers that modulate the response of signaling pathways to extracellular stimuli or stress[8-10]. 4-Hydroxynonenal (HNE), for instance, is a major product generated when free radicals initiate the non-enzymatic fragmentation of PUFAs in biological membranes[5,11]. The levels of HNE and HNE-protein adducts are elevated in cells and tissues exposed to oxidative stress, and HNE can regulate redox-responsive signaling pathways by still poorly understood mechanisms[5,12,13]. 15-deoxy-Δ12,14-prostaglandin J2 (15d-PGJ2) is another LDE produced by a set of enzymes that metabolize arachidonic acid[14]. 15d-PGJ2 exhibits anti-inflammatory and cytoprotective properties and has therefore been designated as a pro-resolving signal[14]. A third example is the LDE 2-trans-hexadecenal (2-HD), which is a product of sphingolipid metabolism and has recently been shown to function as a protein-modifying cofactor that promotes mitochondrial pathways for apoptosis[15]. Understanding the protein targets of LDEs is critical for elucidating their cellular functions and mechanisms of action.

Many drugs and drug candidates also act by covalent modification of cysteine residues, including omeprazole, clopidogrel, and afatinib. The discovery of additional cysteine-reactive chemical probes and drugs would benefit from a general method to globally map compound reactivity with cysteines in native biological systems.

A chemoproteomic method termed isoTOP-ABPP (isotopic Tandem Orthogonal Proteolysis-ABPP) and its use to quantify the intrinsic reactivity of cysteine residues in cell and tissue proteomes has been previously described by certain of the inventors herein[30]. IsoTOP-ABPP measures cysteine reactivity by: 1) treating proteomes with an alkynylated electrophilic iodoacetamide (IA) probe at various concentrations (or for various time periods), 2) conjugation of reactions with isotopically-differentiated azide-biotin tags containing a Tobacco Etch Virus (TEV) cleavage sequence using copper-catalyzed azide-alkyne cycloaddition (CuAAC or click[31]) chemistry, and 3) enrichment, release, and identification/quantitation of IA-labeled cysteine-containing peptides by streptavidin chromatography, TEV protease treatment, and liquid chromatography-high-resolution mass spectrometry (LC-MS), respectively.

SUMMARY

In the present invention, isoTOP-ABPP has been advanced to discover and quantify reactions between cysteines and electrophilic metabolites in proteomes. In this advanced, 'competitive' version of isoTOP-ABPP (FIG. 1*a*), a proteome is treated with an electrophile (experimental sample) or DMSO (control sample). Both proteomic samples are then labeled with the IA probe and conjugated by CuAAC to light and heavy azide-biotin tags, respectively. The light and heavy samples are then mixed and subjected to the previously described isoTOP-ABPP protocol for enrichment, identification, and quantification of IA-labeled cysteines[30]. Electrophile-modified cysteines are quantified by measuring the MS1 chromatographic peak ratios (R values) for heavy (DMSO-treated) over light (electrophile-treated) samples, with higher R values reflecting greater sensitivity to the electrophile. In this format, competitive isoTOP-ABPP can assay electrophiles against 1000+ cysteines in parallel directly in native proteomes without requiring any chemical modification to the electrophiles themselves.

The invention, in various embodiments, is directed to a competitive isoTOP-ABPP method for identifying a protein target of selective cysteine modification by an electrophile, from among a set of proteins of a proteome, cell, tissue, or organism, comprising:

contacting the set of proteins of the proteome and the electrophile to provide an alkylated set of proteins, then, contacting the alkylated set with an alkynylated iodoacetamide probe, followed by reaction with an azido compound comprising a first isotopic marker, to provide an isotopically-marked alkylated set, and contacting the set of proteins of the proteome, not exposed to the electrophile, with an alkynylated iodoacetamide probe, followed by reaction with an azido compound comprising a second isotopic marker, to provide an isotopically-marked control set, then, combining the isotopically-marked alkylated set and the isotopically-marked control set to provide a combined sample, and, identifying the protein target and sites of modification of the electrophile by comparing the abundance of the first isotopic marker and the second isotopic marker for each protein of the set, wherein a target protein for the electrophile possess a relatively higher ratio of the second isotopic marker to the first isotopic marker, compared to an average ratio of second isotopic marker to first isotopic marker among the set of proteins of the combined sample.

The set of proteins can include one or more proteins, such as kinases. A target protein for the lipid-derived electrophiles identified by use of the inventive method has been found to be ZAK kinase. The electrophile can be a stress-induced lipid-derived electrophile such as 4-hydroxynonenal (HNE) or 15-deoxy-Δ12,14-prostaglandin J2. It is believed by the inventors herein that such stress-induced lipid-derived electrophiles act as messenger molecules that modulate the response of signaling pathways to extracellular stimuli or stress; accordingly the identification of the electrophile-targeted protein(s) from among the large number of proteins in a proteome of a cell can serve to identify cellular components that can then be used in the development of modulators for the identified protein, of which ZAK kinase is an example. Such modulators can be used in the control of signaling pathways, such as the activation of mitogen-activated protein kinase (MAPK) pathways including the JNK, ERK, and p38 MAPK pathways that play roles in cancer and inflammation.

It has been discovered by the inventors herein that HNE selectively targets a cysteine residue of ZAK kinase, a mitogen-activated protein kinase kinase kinase (MAP3K) enzyme, in such a way as to confer sensitivity of the MAPK signaling pathways to lipid oxidation products. The identification of ZAK kinase by the method of the invention serves to identify a molecular target for development of ZAK kinase modulators, which can be used to modulate the activity of an MAPK-activating enzyme. Such modulators are believed to have potential as medicinal agents in the treatment of cancer and inflammation.

Figure 1A:
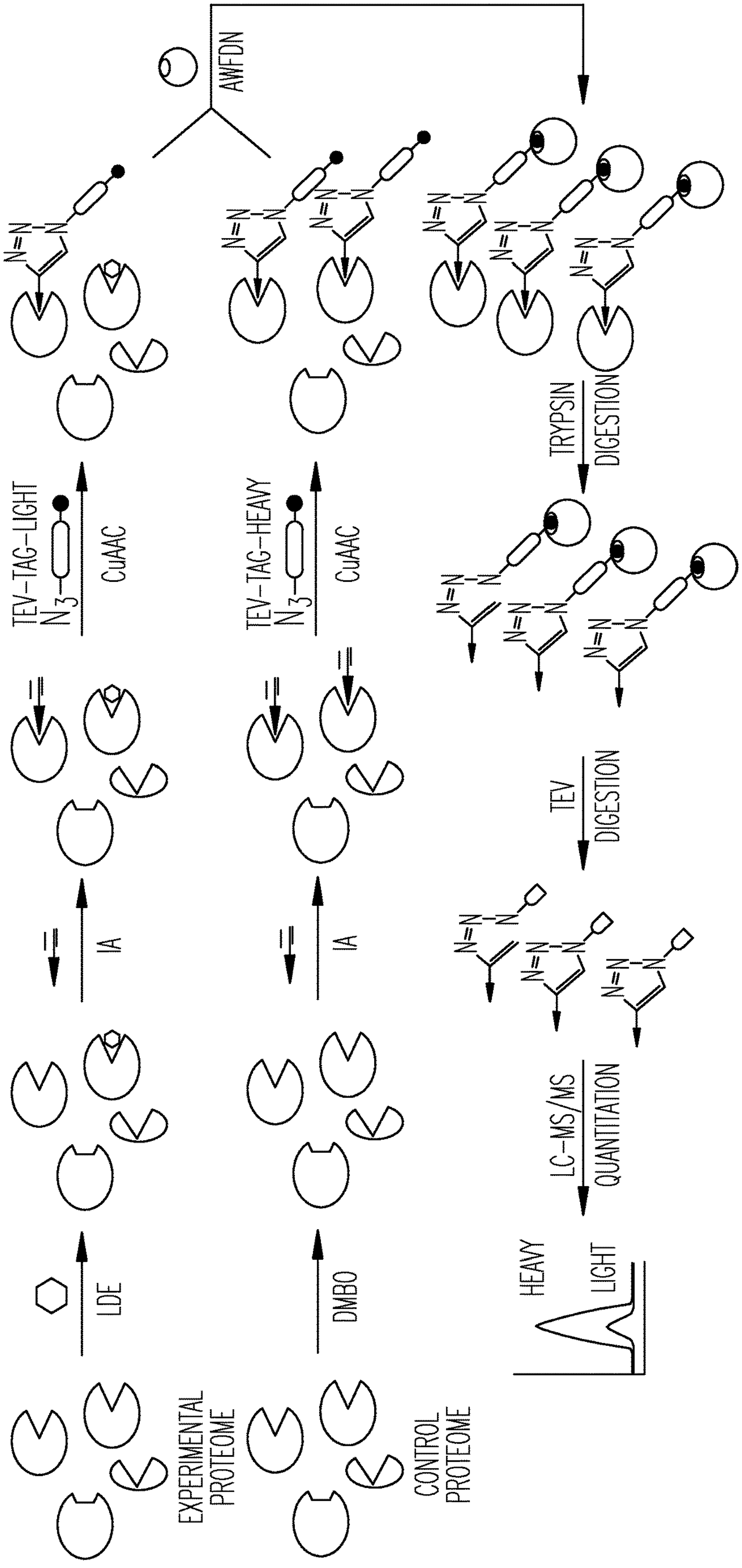
FIG. 1 depicts an embodiment of a competitive isoTOP-ABPP for quantitative mapping of cysteine-reactive, lipid-derived electrophile (LDE) reactions in proteomes. (a) Competitive isoTOP-ABPP involves treatment of proteomes with DMSO or LDE, proteome labeling with an iodoacetamide-alkyne (IA) probe, CuAAC-based incorporation of isotopically-labeled, TEV protease-cleavable biotin tags, enrichment with streptavidin, and sequential on-bead protease digestions to afford probe-labeled peptides for MS analysis. The IA-probe and the competitive blockade of IA-cysteine reactions by an LDE are shown in the inset. (b) Structures of three LDEs, HNE, 15d-PGJ2 and 2-HD, used in competitive isoTOP-ABPP experiments, with their sites of reactivity marked with asterisks.

(a) Distribution of competitive isoTOP-ABPP ratios (R values) quantified from reactions with the human MDA-MB-231 proteome treated with 100 μM HNE (left), 15d-PGJ2 (middle), or 2-HD (right). A cut-off of five-fold or greater blockade of IA-probe labeling (R values>5) is shown by a dashed line to mark cysteines that exhibit high sensitivity to LDEs, and proteins with cysteines showing the strongest competitive reactivity with LDEs are labeled in green. (b) Heat map of cysteines with R values>5 illustrating examples of cysteines that display selectivity for reacting with one of the three tested LDEs (green boxes) and proteins that contain multiple IA-labeled cysteines, only one of which shows sensitivity to LDE competition (red boxes). (c) Representative MS1 profiles for peptides containing cysteines that show selective competition with 15d-PGJ2 (left) or HNE (right). (d) Representative MS1 profiles for multiple cysteine-containing peptides from the same protein, only one of which shows sensitivity to LDE competition. In each example, the LDE-sensitive cysteines is marked in red.

FIG. 3 shows results of determining the potency of HNE-cysteine reactions in proteomes and in cells. (a) Box-and-whisker plots showing the distribution of R values for ~1100 cysteines quantified from competitive isoTOP-ABPP experiments with the MDA-MB-231 proteome treated with 5, 10, 50, 100, and 500 μM HNE. The IA-labeling of cysteines from ZAK, EEF2, RTN4, and FN3KRP exhibit exceptional sensitivity to HNE competition compared to the rest of the cysteines in the proteome. (b) Representative MS1 profiles for HNE-sensitive cysteines in ZAK and RTN4 showing concentration-dependent blockade of IA-labeling by HNE. (c) Distribution of R values quantified from competitive isoTOP-ABPP experiments with proteomes from MDA-MB-231 cells treated in situ with DMSO or HNE (100 μM, 60 min), confirming that cysteines in ZAK, EEF2, RTN4 and FN3KRP are also highly sensitive to HNE competition in living cells. (d) Comparison of R values obtained from in vitro versus in situ competitive isoTOP-ABPP experiments. Red and black diamonds mark cysteines that show similar or different in vitro versus in situ R values, respectively.

FIG. 4 depicts the functional characterization of HNE modification of ZAK kinase. (a) Crystal structure of human MAP3K9 (left, PDB: 3DTC) and multiple sequence alignment of ZAK with other 19 human MAP3Ks (SEQ ID NOs: 27-46) showing the HNE-sensitive cysteine C22 of ZAK is located next to the kinase's ATP binding loop ("P-loop"; note that C22 corresponds to 1150 in MAP3K9) and is unique to ZAK relative to other MAP3K enzymes. (b) Selective IA-labeling of wild-type (WT), but not C22A-ZAK, and concentration-dependent competition of IA-labeling of WT-ZAK by HNE as measured by gel-based ABPP using an IA-rhodamine probe. ZAK were expressed as FLAG-tagged proteins in HEK293T cells by stable transfection and immunoprecipitated prior to IA-probe labeling and analysis. (c) An HNE-alkyne probe (HNEyne16) selectively labels WT-, but not C22A-ZAK in proteomes and in living cells as determined by gel-based ABPP. (d) Catalytic activity of immunoprecipitated WT-, but not C22A-ZAK is inhibited by HNE as measured using a Myelin Basic Protein (MBP) substrate assay. A K45M-ZAK mutant, in which a conserved active-site lysine was mutated, showed no detectable activity and thus served as a catalytically dead control enzyme. All three ZAK variants (WT, C22A, and K45M were expressed at similar levels in transfected HEK293T cells). (e) Quantitative profiling of kinase activities in ZAK-transfected HEK293T proteomes treated with DMSO or HNE (100 μM, 30 min) by SILAC-ABPP using an acylphophate-ATP probe shows that the ATP-binding of ZAK is greatly impaired by HNE modification on C22. Other kinases detected in this assay were, in general unaffected by HNE treatment. For (d) and (e), data are presented as mean values±SEM; N>=3 experiments/group. , P<0.01, *, P<0.001, t-test.

FIG. 5 shows that HNE modification of ZAK suppresses JNK pathway activation in cells. (a) WT-ZAK-transfected HEK-293T cells show higher basal JNK activation compared to mock-, C22A-ZAK-, or K45M-ZAK-transfected. (b), (c) Western blots (b) and normalized phosphorylated JNK levels (c) showing that $H_2O_2$ treatment (1 mM, 30 min) increases JNK activation in WT- and C22A-ZAK cells and this increase is blocked or amplified in WT- and C22A-ZAK cells, respectively by pre-treatment with HNE (100 μM, 30 min) (d) A model diagramming ZAK-dependent and ZAK-independent pathways for HNE modulation of JNK activation. Dashed line designates the potential for oxidative stress to generate HNE and initiate a negative feedback loop to limit JNK activation. (e), (f) Western blots (e) and normalized phosphorylated JNK levels (f) showing dramatic, concentration-dependent activation of JNK by HNE (50 or 100 μM, 60 min) in C22A-ZAK cells, but not in WT-ZAK cells. Note that mock- and K45M-ZAK transfected cells also show modest, but significant elevations in JNK activity following HNE treatment, which is consistent with previous studies indicating that HNE can activate JNK by multiple pathways[42,43,57]. For (a), (c) and (f), data are presented as mean values±SEM; N=4 experiments/group. *, $P<0.05$, **, $P<0.01$##, $P<0.01$, t-test.

DETAILED DESCRIPTION

A competitive isotopic Tandem Orthogonal Proteolysis Activity-Based Protein Profiling (isoTOP-ABPP) method for quantifying the reactivity of electrophilic compounds against 1000+ proteins comprising reactive cysteines in parallel in the human proteome is disclosed and claimed herein. Using this approach, we identify select sets of proteins that are preferentially modified by HNE and 15d-PGJ2. We show that one of these proteins, ZAK kinase, is labeled (alkylated) by HNE on a conserved, active site-proximal cysteine residue, which inhibits the enzyme and suppresses the activation of JNK pathways by oxidative stress in cancer cells.

The invention provides, in various embodiments, a competitive isoTOP-ABPP method for identifying a protein target of selective cysteine modification by an electrophile, from among a set of proteins of a proteome, cell, tissue, or organism, comprising:

contacting the set of proteins of the proteome and the electrophile to provide an alkylated set of proteins, then, contacting the alkylated set with an alkynylated iodoacetamide probe, followed by reaction with an azido compound comprising a first isotopic marker, to provide an isotopically-marked alkylated set, and contacting the set of proteins of the proteome, not exposed to the electrophile, with an alkynylated iodoacetamide probe, followed by reaction with an azido compound comprising a second isotopic marker, to provide an isotopically-marked control set, then, combining the isotopically-marked alkylated set and the isotopically-marked control set to provide a combined sample, and, identifying the protein target and sites of modification of the electrophile by comparing the abundance of the first isotopic marker and the second isotopic marker for each protein of the set, wherein a target protein for the electrophile possess a relatively higher ratio of the second isotopic marker to the first isotopic marker, compared to an average ratio of second isotopic marker to first isotopic marker among the set of proteins of the combined sample.

For example, the set of proteins can include one or more proteins, such as ZAK kinase.

The electrophile can be a lipid derived electrophile, such as a stress-induced electrophile, wherein the protein target of the electrophile is a kinase. The kinase can comprise a cysteine residue that is alkylated by the electrophile, and when the electrophile comprises an α,β-unsaturated carbonyl group, such as 4-hydroxynonenal or 15-deoxy-Δ12,14-prostaglandin J2, the electrophile can react with the cysteine by a Michael conjugate addition.

By identification of a protein target of an electrophile, the protein target of the electrophile can be used as a substrate for identification of further inhibitors thereof, by screening a plurality of candidate compounds for modulation of the kinase protein target to identify one or more selective kinase modulator. A selective kinase modulator is a potential medicinal compound for treatment of a condition wherein modulation, e.g., inhibition, of the kinase activity is medically indicated. For example, a selective modulator of the kinase protein target so identified can be a reversible inhibitor of the kinase protein target, which can be suitable for development as a medicament for treatment of the condition in human beings, e.g., for treatment of cancer or of inflammation.

The invention also provides, in various embodiments, a protein identified as a target of an electrophile by the method of the invention. The protein can be a kinase, such as ZAK kinase, and can be used for the development of kinase modulators, e.g., a ZAK kinase inhibitor suitable for administration to a human subject suffering from a condition such as cancer or inflammation wherein modulation of the kinase is medically indicated.

Quantitative Profiling of Electrophile-Cysteine Reactions in Proteomes.

Among the 20 protein-coding amino acids, cysteine is unique owing to its intrinsically high nucleophilicity, which renders its sensitivity to modification by endogenous electrophiles and oxidants[6], as well as electrophilic xenobiotics and candidate therapeutics[23,24]. Cysteine reactions with electrophilic metabolites have been characterized for purified proteins.[25,26] and, on a global scale in cells and tissues using mass spectrometry-based chemoproteomic[5,16-22] and imaging methods[27]. These studies, along with analytical, quantum mechanical, and kinetic work[28,29], have, for the most part, confirmed the preferential reactivity that Michael acceptor electrophiles like HNE show for cysteine over other potentially nucleophilic amino acids (e.g., lysine, histidine) in proteomes. We were interested in building on these past findings to determine whether individual cysteines in the proteome display differences in their reactivity with endogenous electrophiles, and, if so, whether potential hotspots for electrophile modification might constitute key nodes in signaling pathways of redox sensing and response.

We previously described a chemoproteomic method termed isoTOP-ABPP (isotopic Tandem Orthogonal Proteolysis-ABPP) and its use to quantify the intrinsic reactivity of cysteine residues in cell and tissue proteomes[30]. isoTOP-ABPP measures cysteine reactivity by: 1) treating proteomes with an alkynylated electrophilic iodoacetamide (IA) probe at various concentrations (or for various time periods), 2) conjugation of reactions with isotopically-differentiated azide-biotin tags containing a Tobacco Etch Virus (TEV) cleavage sequence using copper-catalyzed azide-alkyne cycloaddition (CuAAC or click[31]) chemistry, and 3) enrichment, release, and identification/quantitation of IA-labeled cysteine-containing peptides by streptavidin chromatography, TEV protease treatment, and liquid chromatography-high-resolution mass spectrometry (LC-MS), respectively.

Here, we envisioned that isoTOP-ABPP could be advanced to discover and quantify reactions between cysteines in proteomes and any electrophilic compound. In this advanced, 'competitive' version of isoTOP-ABPP (FIG. 1*a*), a proteome is treated with an electrophile (experimental sample) or DMSO (control sample). Both proteomic samples are then labeled with the IA probe and conjugated by CuAAC to light and heavy azide-biotin tags, respectively. The light and heavy samples are then mixed and subjected to our described isoTOP-ABPP protocol for enrichment, identification, and quantification of IA-labeled cysteines[30]. Electrophile-modified cysteines are quantified by measuring the MS1 chromatographic peak ratios (R values) for heavy (DMSO-treated) over light (electrophile-treated) samples, with higher R values reflecting greater sensitivity to the electrophile. In this format, competitive isoTOP-ABPP can assay electrophiles against 1000+ cysteines in parallel directly in native proteomes without requiring any chemical modification to the electrophiles themselves.

Figure 1B:
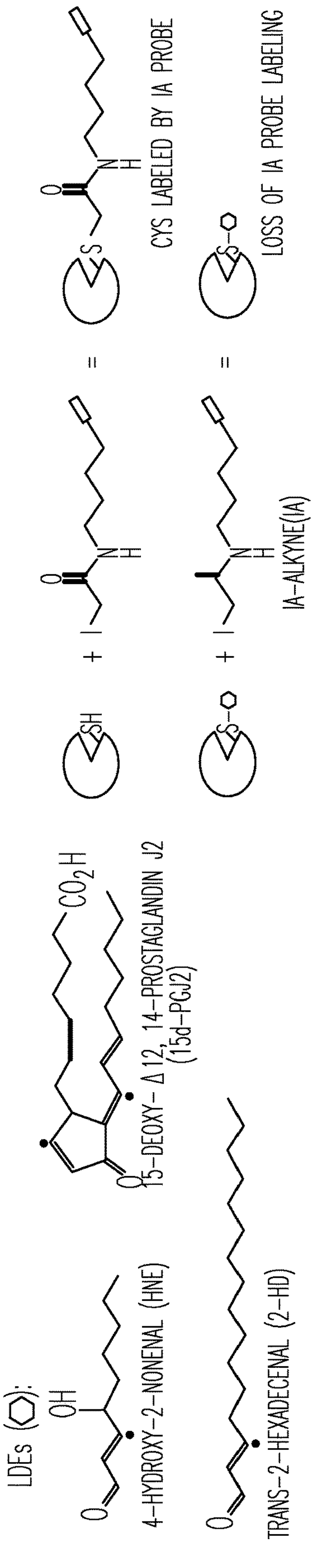
Figure 2A:
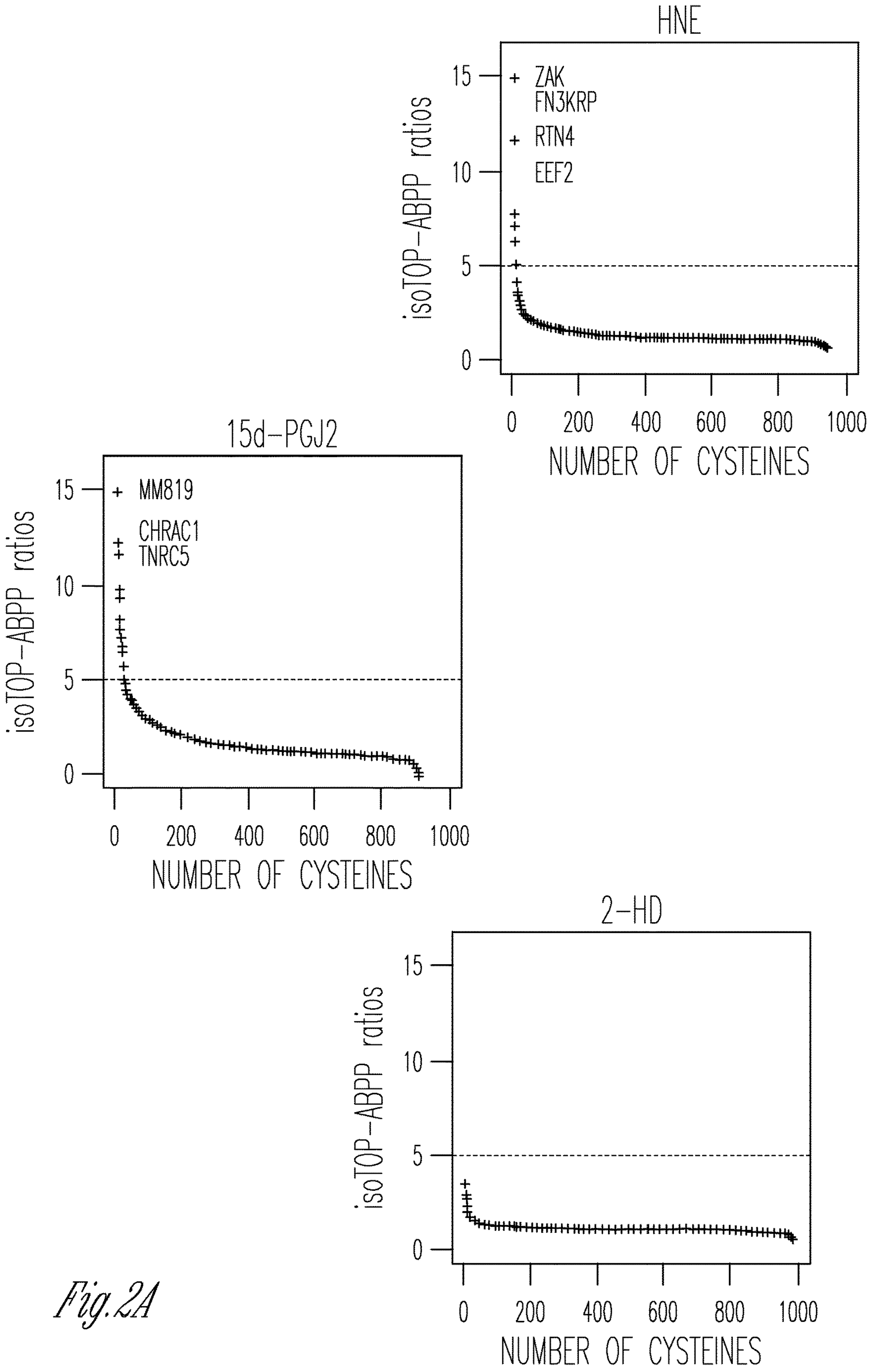
FIG. 2 depicts results of quantitative profiling of LDE-cysteine reactions in proteomes.
Figure 2B:
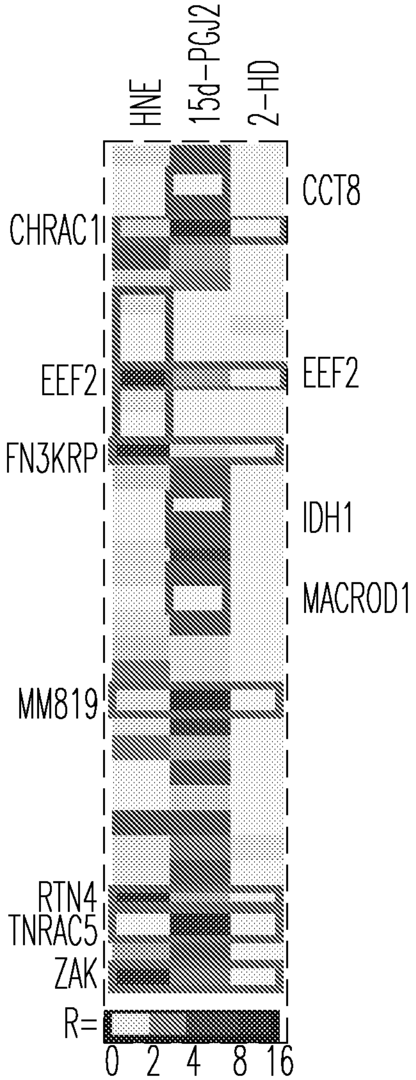

We applied competitive isoTOP-ABPP to quantitatively profile the proteome reactivity of three representative endogenous electrophiles—HNE, 15d-PGJ2, and 2-HD, each of which possesses an α,β-unsaturated carbonyl that can react with nucleophilic cysteines via Michael addition (FIG. 1*b*). Competitive isoTOP-ABPP experiments were performed in quadruplicate using the soluble proteome of the human breast cancer cell line MDA-MB-231 cell line. Proteomes were treated with 100 μM HNE, 15d-PGJ2, or 2-HD, for 60 minutes, followed by the IA-probe (100 μM, 60 min) A total of ~1400 cysteine reactivities were quantified across the aggregate data set, with at least 900 cysteine reactivities quantified for each LDE (FIG. 2*a*) more than 750 of which were quantified for all the three electrophiles. Most of the cysteine reactivities (>98%) were unaffected or only marginally affected by LDE treatment (R<5); however, a select subgroup showed marked reductions in their IA-probe reactivities (R>5) following exposure to one or more LDEs (FIG. 2*a*). A closer examination of these LDE-inhibited cysteines revealed a distinct proteome reactivity profile for each tested electrophile, with HNE and 15d-PGJ2 both targeting several cysteines in the proteome, the majority of which showed preferential reactivity with one of the two LDEs, and 2-HD exhibiting no detectable high sensitivity (R>5) targets (FIG. 2*a*).

Figure 2C:
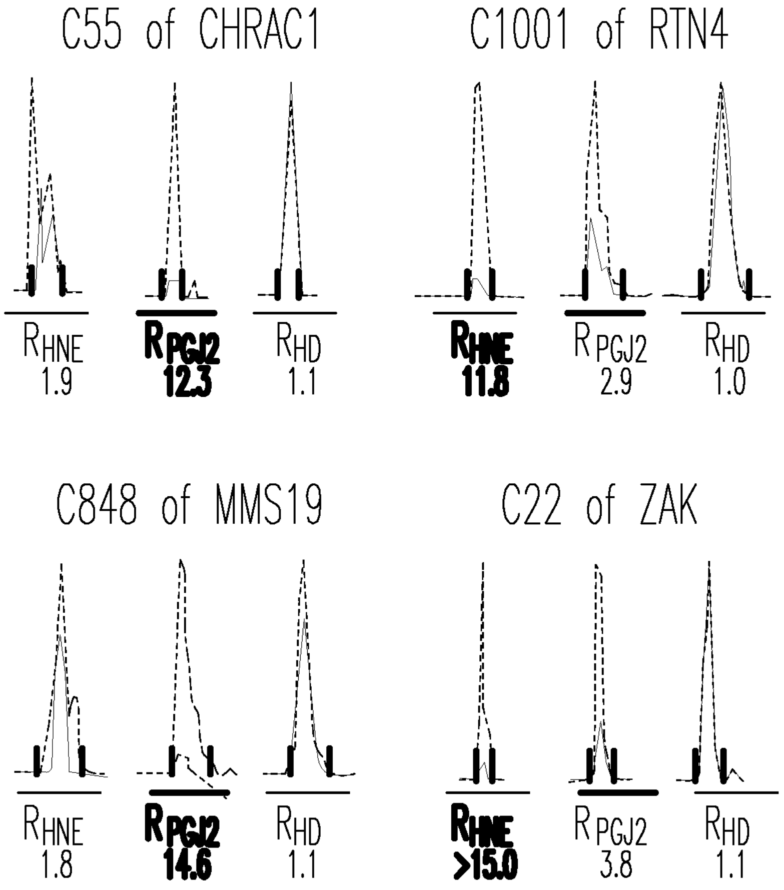
Figure 2D:
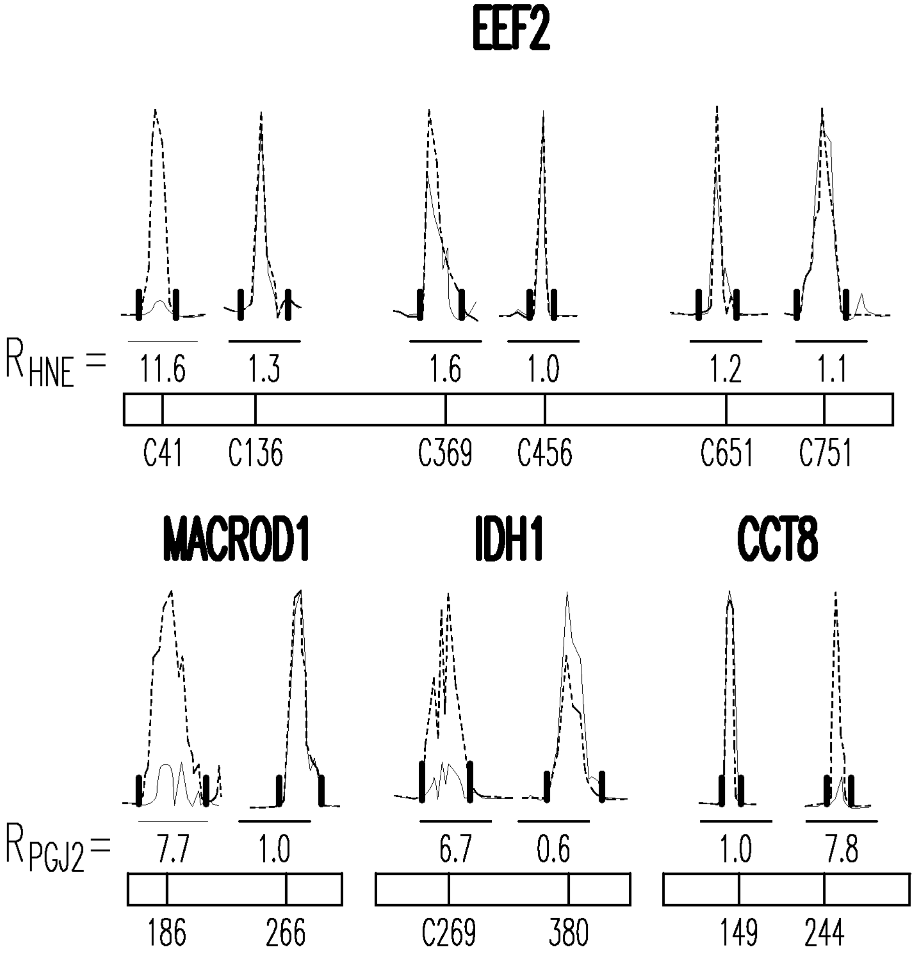

The quantitative ranking of cysteines based on the magnitude and selectivity of their inhibition illuminated "hot spots" for LDE reactivity in the proteome (FIG. 2*a* and Table 1). Examples included Cys22 of ZAK (or MLTK/MLK7) and Cys848 of MMS19, which were completely blocked with notable selectivity by FINE and 15d-PGJ2, respectively (FIG. 2*c*). Competitive isoTOP-ABPP also identified several proteins that possess multiple reactive cysteines, only one of which proved sensitive to competitive blockade by an LDE (FIG. 2*d*). These data demonstrate that the quantified R values reflect measurements of individual LDE-cysteine reactions rather than general changes in protein abundance potentially caused by LDE exposure. In this regard, we did not observe any instances of multiple LDE-sensitive cysteines appearing on the same protein (see Table 1, below). We also asked whether the intrinsic reactivity of cysteines, as determined previously by measuring their extents and rates of IA labeling[30], might be predictive of sensitivity to LDEs. However, we found that most of the LDE-sensitive cysteines displayed moderate, rather than high IA-reactivity, suggesting that their modification by LDEs depend not only on cysteine nucleophilicity, but also on molecular recognition of the LDEs.

Determining the Potency of HNE-Cysteine Reactions in Proteomes

Having found that individual LDEs show markedly distinct cysteine-reactivity profiles, we next focused on identifying the most sensitive sites for LDE reactivity in the proteome by performing a concentration-dependent analysis with HNE. The MDA-MB-231 cell proteome was treated with varying concentrations of HNE (5, 10, 50, 100 and 500 μM) for 60 min and then the IA-labeling profile of each reaction was quantitatively compared to a DMSO-control sample by isoTOP-ABPP. In aggregate, these profiles identified ~1100 IA-labeled cysteines, many of which showed reduced labeling signals in the presence of HNE, including 8 of the 14 HNE-modified cysteines identified in a previous proteomic study that used a biotinamidohexanoic acid hydrazide probe to enrich and identify (but not to quantify) HNE-modified cysteines[17].

Figure 3A:
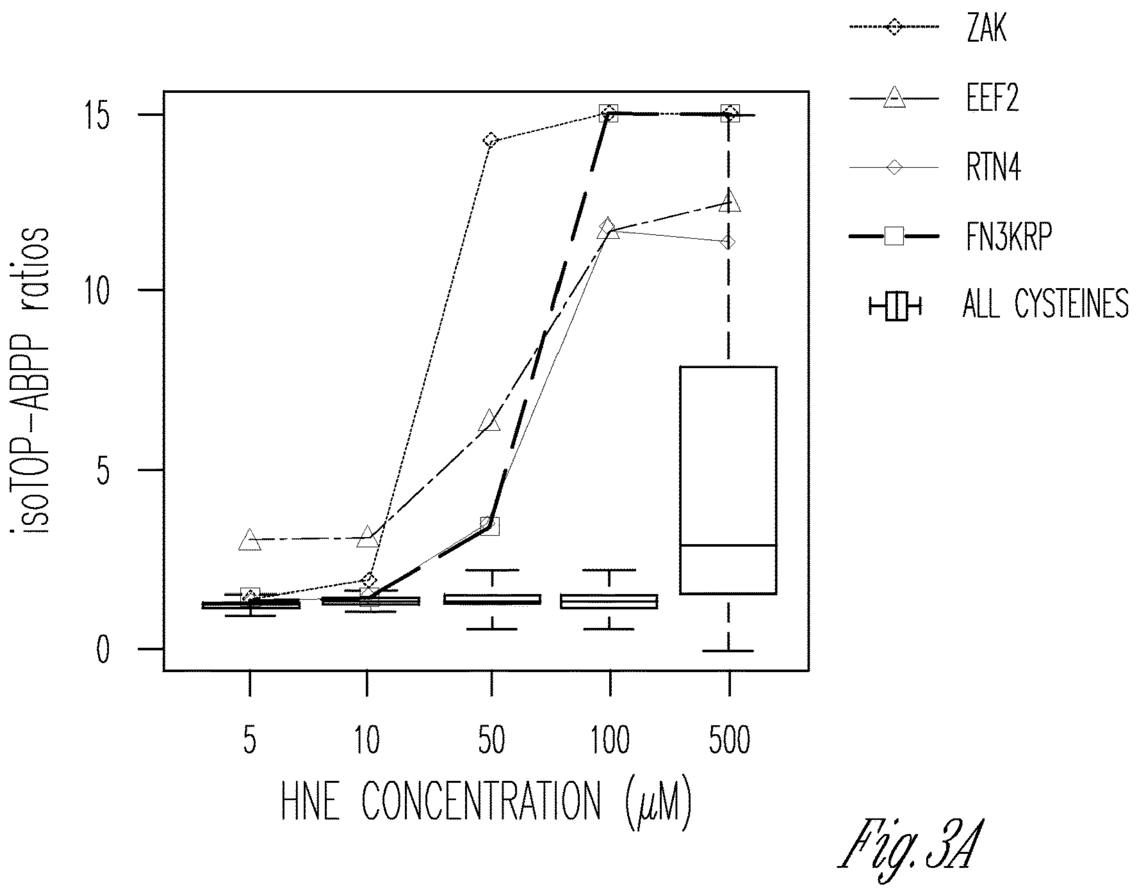
Figure 3B:
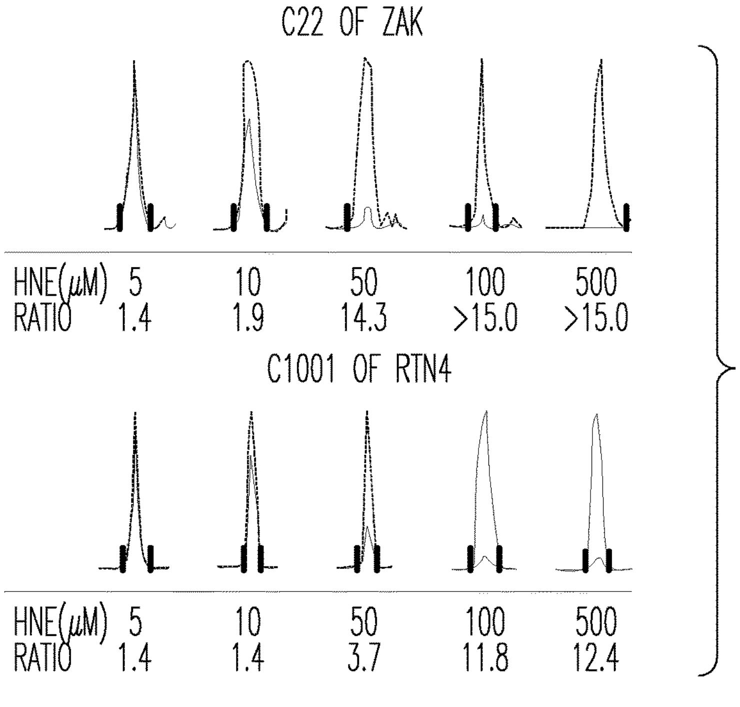
Figure 3C:
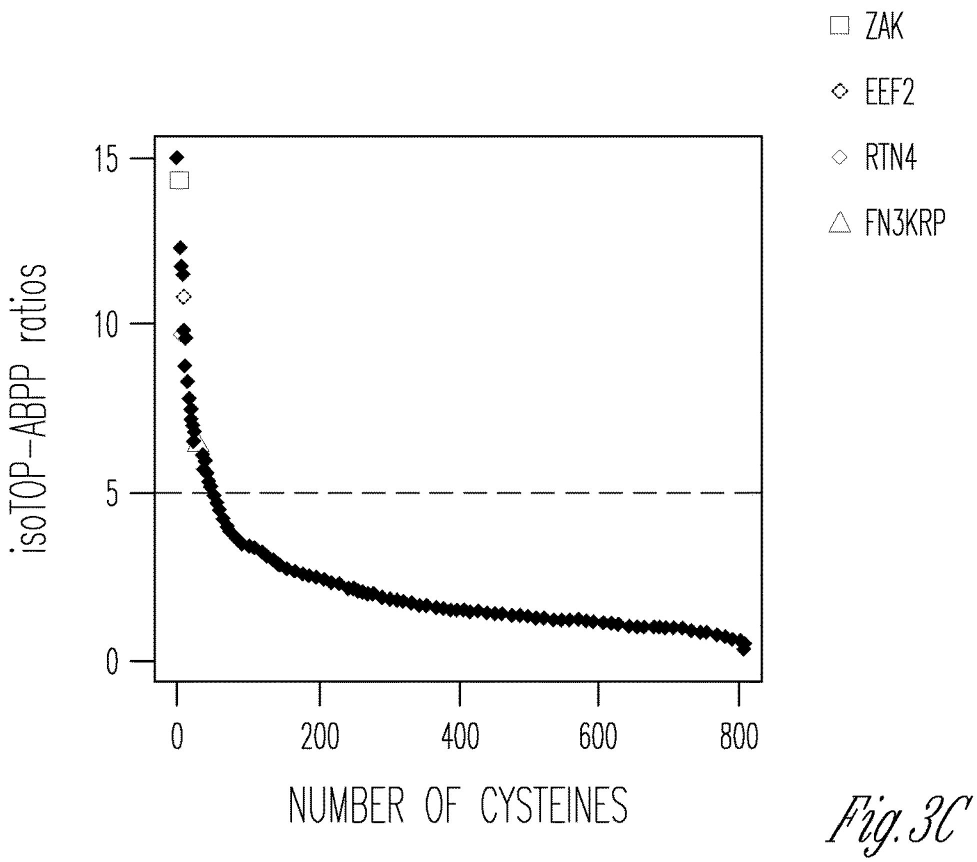
Figure 3D:
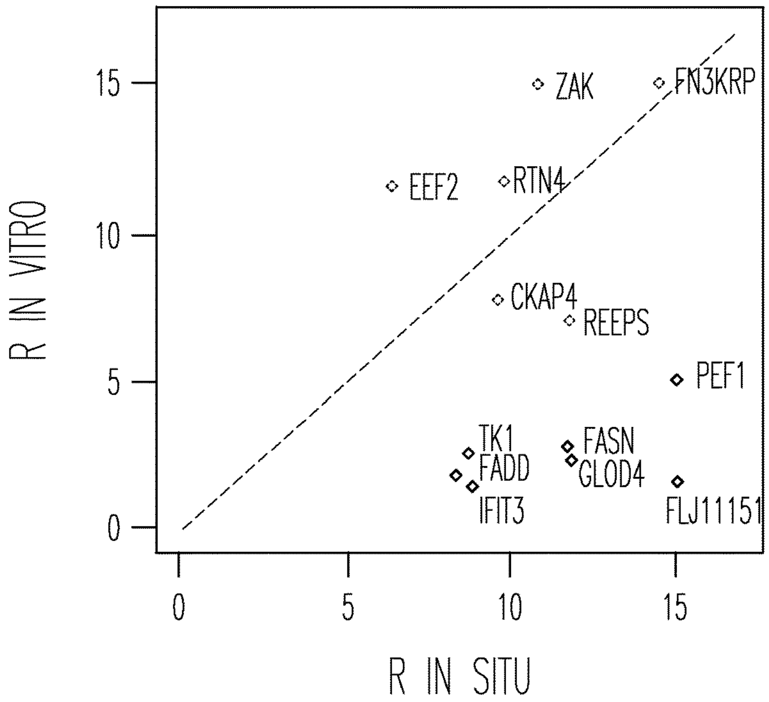

By combining the R values at all 5 HNE concentrations, we could extrapolate IC50 values for FINE-blockade of IA probe-labeling for ~700 of the 1100 cysteines (FIG. 3*a*). This analysis revealed that the vast majority of cysteines were modified by HNE with low potency (IC50 values>100 μM), but a select few cysteines, including C22 of ZAK, C41 of EEF2, C24 of FN3KRP, and C1001 of RTN4, exhibited much higher sensitivities with IC50 values ranging from 6 to 23 μM (FIG. 3*a, b*). We next tested whether these hypersensitive cysteines were also inhibited by HNE in situ by treating MDA-MB-231 cells with 50 or 100 μM HNE and then preparing proteomes for analysis by competitive isoTOP-ABPP. These experiments confirmed that the most HNE-sensitive cysteines identified in vitro were also strongly inhibited by HNE in situ (FIG. 3*c, d*). We also uncovered another set of cysteines that showed reductions in IA-probe labeling in situ, but not in vitro (FIG. 3*d*, black diamonds). This finding suggests that certain proteins may preferentially react with HNE in living cells, although we cannot exclude at this point that the reductions in IA probe labeling observed for these proteins reflect a decrease in their overall abundance in HNE-treated cells.

Functional Characterization of HNE Modification of ZAK Kinase

ZAK kinase (also known as MLK7 or MLTK) is part of the mitogen-activated protein kinase (MAPK) network and functions as a MAPK kinase kinase (MAP3K)[32,33]. There are at least 20 MAP3Ks encoded by the human genome and they are activated by diverse stimuli to phosphorylate and activate downstream MAPK kinases (MAP2Ks) to regulate critical cellular functions, such as differentiation, proliferation and apoptosis[34]. Previous studies have shown that ZAK can activate all three major MAPK (ERK, JNK, and p38) pathways in mammalian cells,[32,35,36] with some preference for JNK[32] and is involved in response pathways to stressors such as osmotic shock[33], UV radiation[37], and chemotherapeutic agents[36]. Sequence and structure comparisons allowed us to map the HNE-sensitive cysteine in ZAK (C22) to a location proximal to the glycine-rich ATPbinding loop ("P-loop") (FIG. 4*a*). Interestingly, among all 20 human MAP3Ks, ZAK is the only member that possesses a cysteine at this position (FIG. 4*a*), and this cysteine is highly conserved across ZAK orthologues in vertebrates.

Figure 4B:
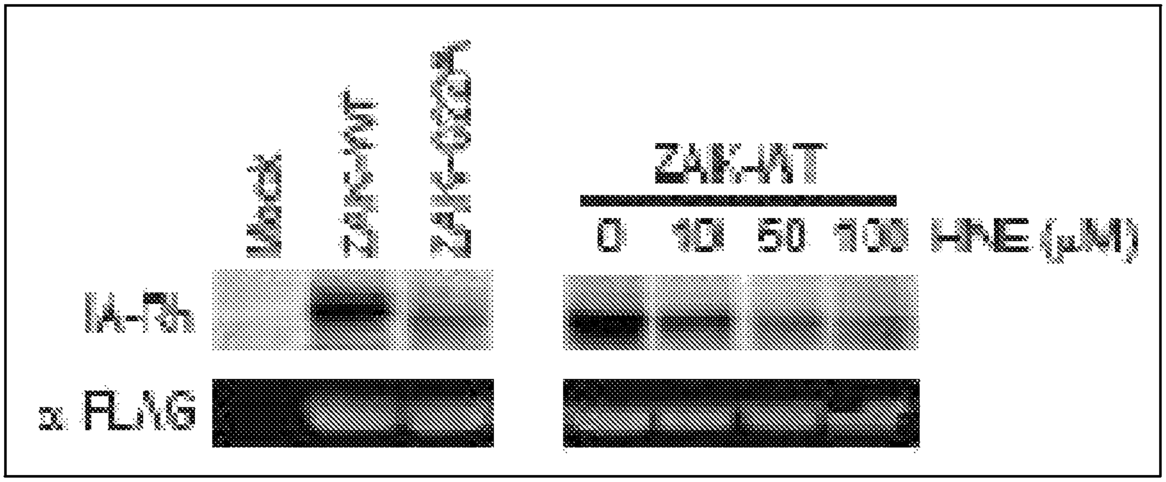
Figure 4C:
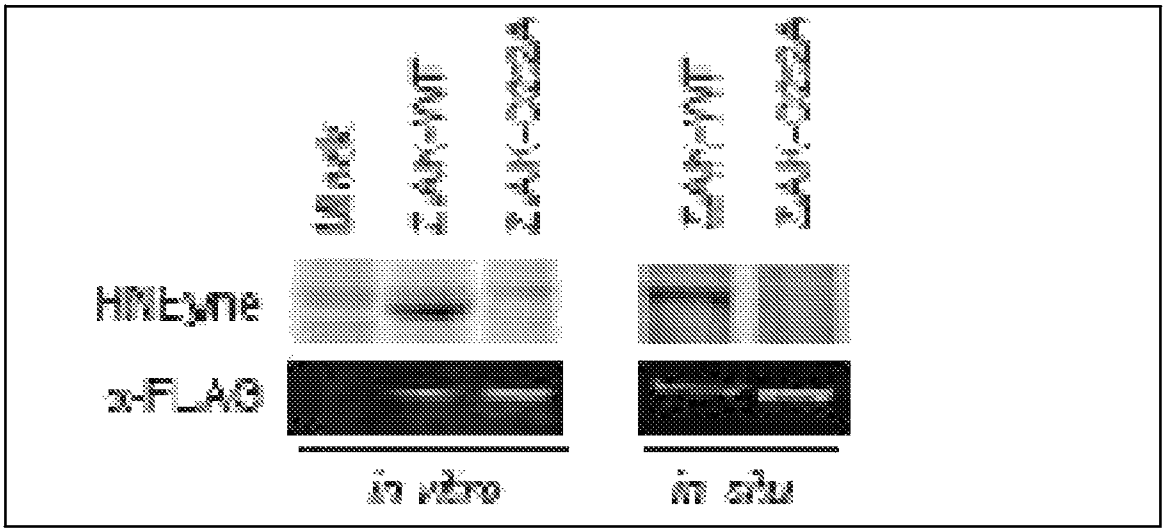
Figure 4D:
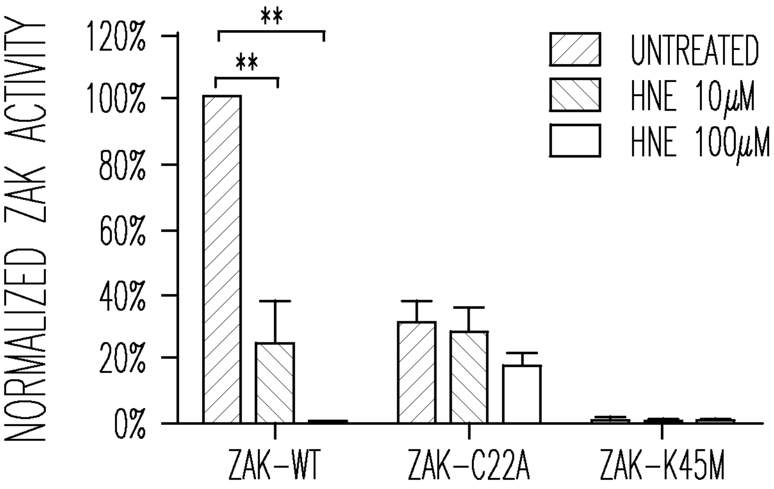
Figure 4E:
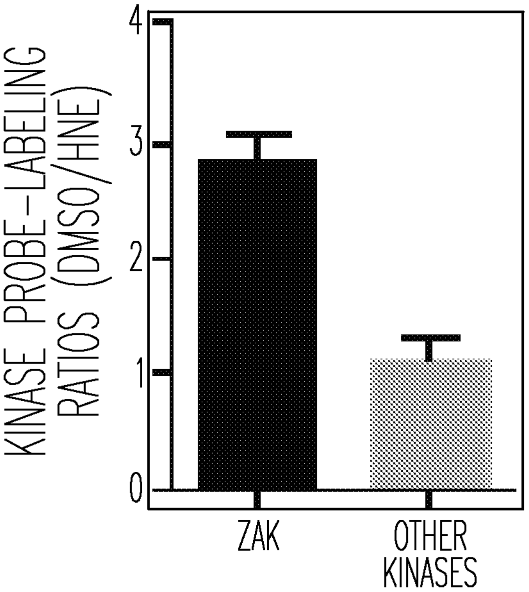

This information, combined with the high sensitivity displayed by C22 for HNE (FIG. 3*a*) motivated us to further characterize this interaction and its impact on ZAK activity. We first expressed FLAG-tagged versions of wild type (WT) and a C22A mutant of ZAK by stable transfection in HEK293T cells and found that WT-ZAK showed much stronger IA-rhodamine probe labeling as measured by gel-based ABPP. This result is consistent with our isoTOP-ABPP data sets, which identified C22 as the most IA-reactive cysteine in ZAK30. The gel signals for IA-labeling of WT-ZAK were blocked by pretreatment with HNE over a concentration range that closely matched the HNE-sensitivity profile observed for C22 in competitive isoTOP-ABPP experiments (FIG. 4*b*, compare to FIG. 3*a*). Given that competitive isoTOP-ABPP measures blockade of IA-labeling of cysteines by LDEs, we next used an alkyne-functionalized HNE probe (HNEyne)[16] to verify direct labeling of WT-, but not the C22A-ZAK mutant in vitro and in living cells (FIG. 4*c*). We then assessed the impact of HNE labeling on ZAK activity using an in vitro Myelin Basic Protein (MBP) substrate assay[38] which showed that HNE inhibited WT-, but not C22A-ZAK in a concentration-dependent manner (FIG. 4*d*). We note that C22AZAK exhibited reduced basal activity compared to WT-ZAK, but the residual activity of C22-ZAK, which was still much greater than a catalytically dead K45M-ZAK mutant, was insensitive to HNE (FIG. 4*d*). Taken together, these data indicate that C22 contributes to the intrinsic catalytic activity of ZAK and reaction of this residue with FINE produces complete inhibition of the kinase. Considering further that C22 is predicted to reside adjacent to the ATP-binding loop of ZAK, we postulated that the HNE-induced loss of kinase activity might be due to blockade of ATP-binding. We tested this hypothesis by performing a competitive SILAC (Stable Isotope Labeling by Amino acids in Cell culture)-ABPP39 experiment using an acylphosphate-ATP probe[40], which revealed that probe-labeling of ZAK, but not other kinases, was profoundly reduced in cell proteomes treated with HNE (FIG. 4*e*).

HNE Modification of ZAK Suppresses JNK Pathway Activation in Cells

Figure 5A:
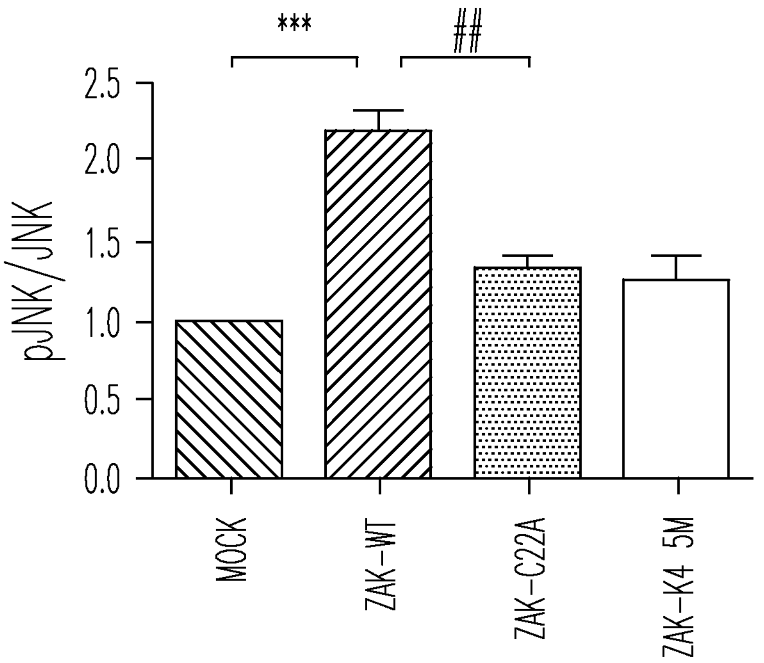
Figure 5B:
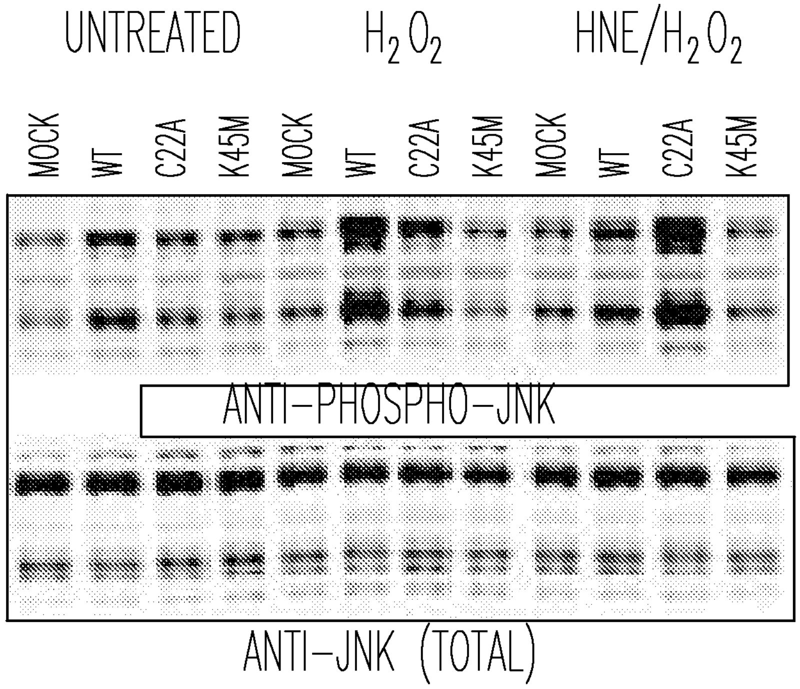
Figure 5C:
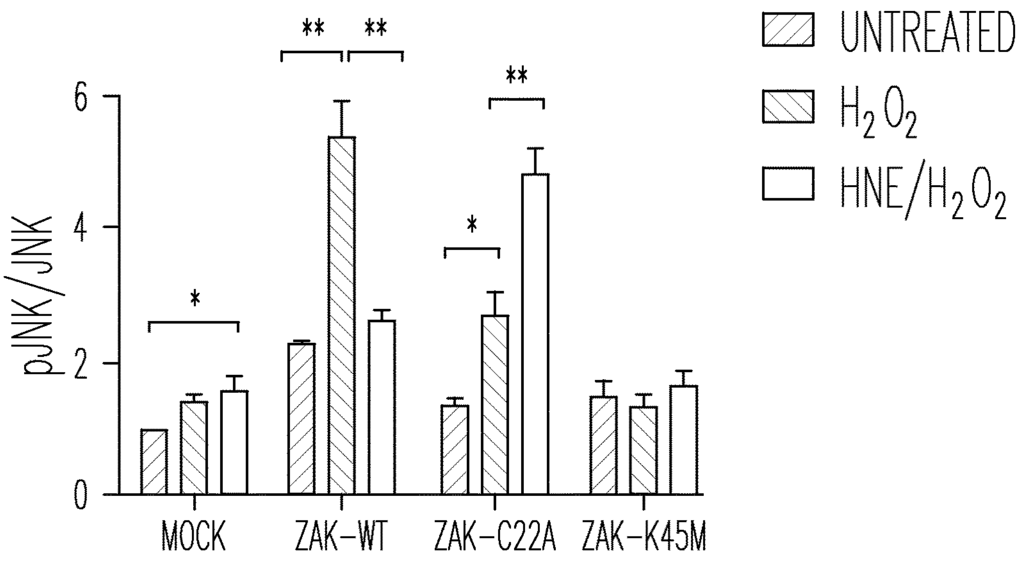
Figure 5D:
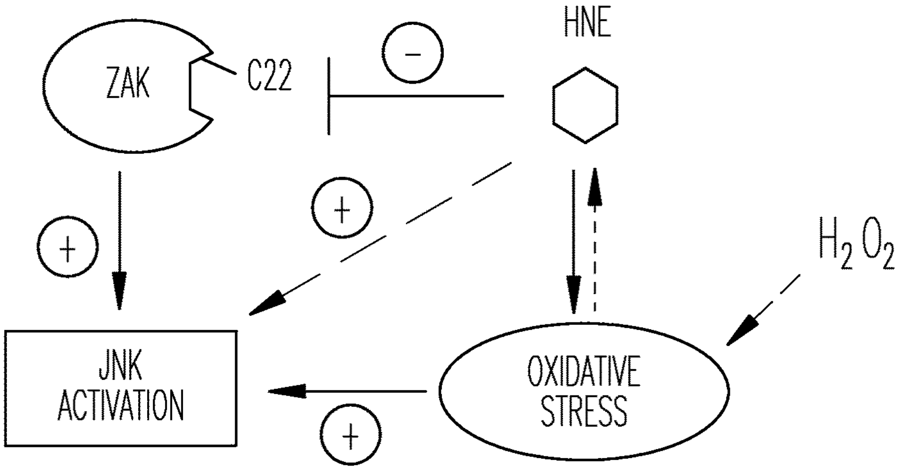
Figure 5E:
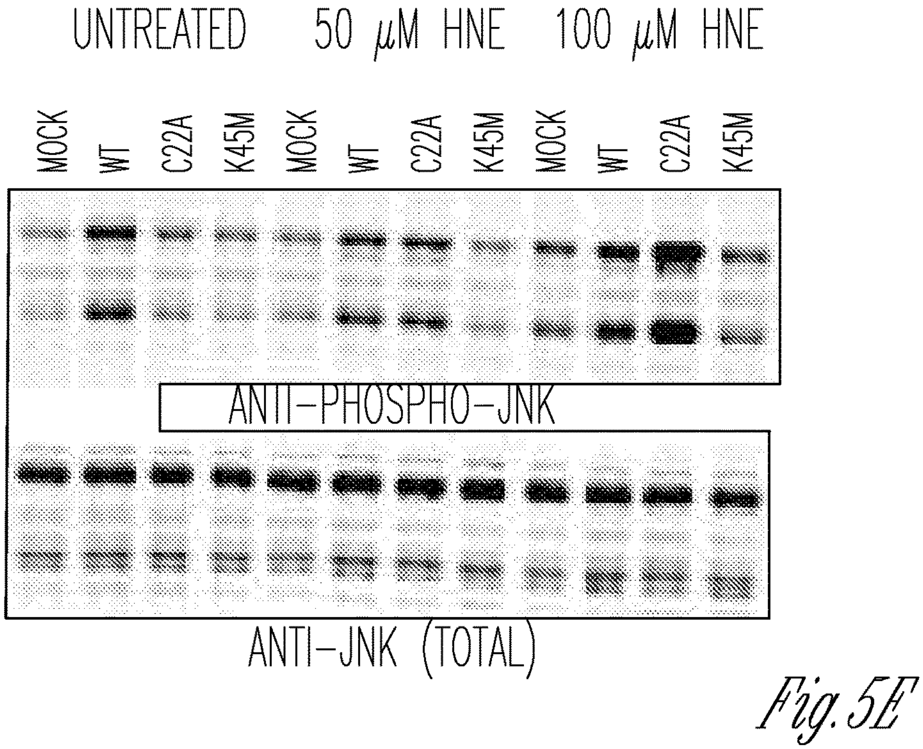
Figure 5F:
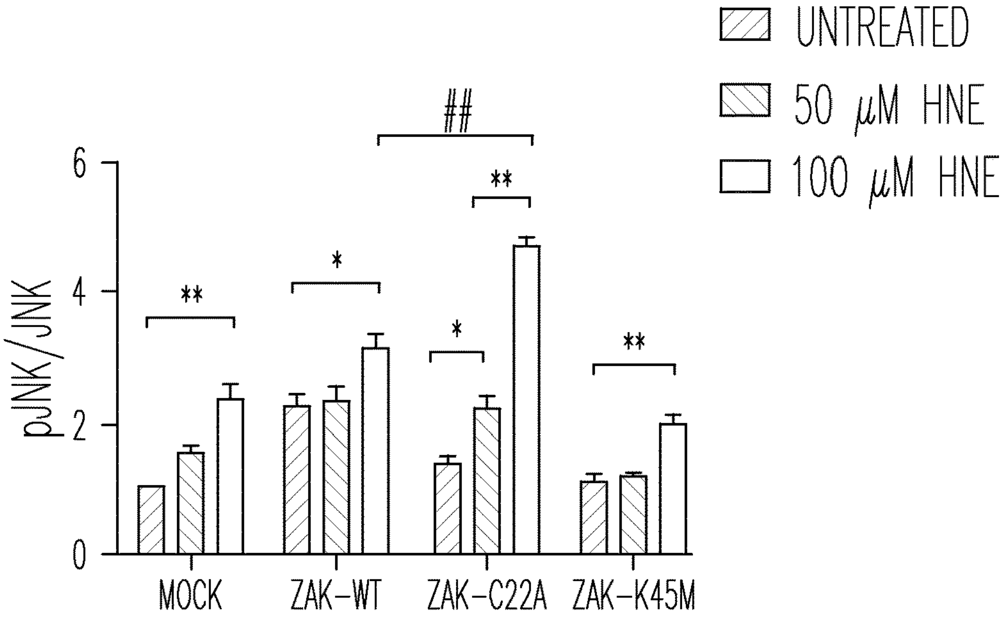

We next set out to assess the functional effects of HNE modification of ZAK in human cells. HEK-293T cells were stably transfected with cDNAs for WT-ZAK, C22A-ZAK, or K45M-ZAK and the activation state of their MAPK signaling pathways was monitored by western blotting with anti-phosphoprotein antibodies. WT-ZAK-expressing cells, but not C22A- or K45M-ZAK-expressing cells showed significantly increased JNK and, to a lesser extent, p38 and ERK pathway activation compared to mock-transfected cells (FIG. 5*a, b*). These cellular data are consistent with previous studies showing that over-expression of WT-ZAK in mammalian cells preferentially activates the JNK pathway[32] and with our in vitro substrate assay results, which revealed substantially reduced and complete loss of activity for the C22A- and K45M ZAK mutants, respectively (FIG. 4*d*). We next treated cells with $H_2O_2$ (1 mM, 30 min) to induce oxidative stress, a process that is known to activate the JNK pathway[41,42]. $H_2O_2$ treatment stimulated JNK activity in both WT- and C22A-ZAK-transfected cells (but not K45M-ZAK-transfected cells), with WT-ZAK cells showing the greater level of activation (FIG. 5*b,c*). Strikingly, however, pre-treatment with HNE (100 μM, 30 min) produced opposing effects in WT- and C22A-ZAK cells, blocking $H_2O_2$-dependent JNK activation in the former cell model, while hyper-activating JNK activity in the latter. We interpret these findings to indicate the existence of both ZAK-dependent and ZAK-independent pathways for HNE modulation of JNK activation (FIG. 5*d*). By modifying C22 on ZAK, HNE blocks the contribution that this kinase makes to the activation of the JNK pathway. HNE is also known to itself promote oxidative stress[43,44] that likely adds to the effects of $H_2O_2$ and, in the context of an HNE-resistant C22A-ZAK mutant, would serve to further augment activation of the JNK pathway. In this model, the HNE-ZAK interaction acts as a negative-feedback loop that tempers activation of the JNK pathway under high and/or persistent levels of oxidative stress (FIG. 5*d*). We further tested this idea by evaluating the effects of HNE alone on JNK pathway activity in ZAK-transfected cells. A dramatic concentration-dependent activation of JNK was observed in C22A-ZAK-transfected cells, but not in WT-ZAK-transfected cells, which showed higher basal JNK activation that was mostly unaffected by HNE (FIG. 5*e,f*). While we were initially surprised that HNE treatment did not appear to block the basal JNK activation caused by WT-ZAK, we should note that HNE also activated JNK in mock-transfected cells to a level that matched the basal JNK activity observed in WT-ZAK-transfected cells. Thus, the residual JNK activation observed in WT-ZAK-transfected cells may reflect ZAK-independent pathways of JNK activation by HNE (FIG. 5*e,f*). That JNK activation was much higher in C22A-ZAK cells compared to the other cell models indicates this HNE-insensitive form of ZAK, which still retains some catalytic activity (see FIG. 4*d*), combines with ZAK-independent, HNE-stimulated pathways to further enhance JNK activation.

Long viewed as biomarkers of oxidative damage, LDEs have more recently gained attention as second messengers that can regulate diverse cellular processes[8,9]. These findings have inspired the advent of chemoproteomic methods to globally map LDE-protein interactions[5,16-19]. To date, these large-scale profiling efforts have focused on the qualitative inventorying of LDE-reactive proteins in cell and tissue proteomes, generating lists of many candidate targets and pathways for LDE action. Considering, however, that the signaling and pathophysiological functions of LDEs may differ across the endogenous concentration ranges found for these compounds, it is imperative to understand the potencies of LDE-protein interactions in biological systems. Building on past studies showing that cysteine residues are the principal sites of protein modification by HNE[28,29], we created a competitive isoTOP-ABPP platform to quantitatively map LDE reactivity across 1000+ cysteines in parallel directly in native proteomes. The output of this study was the identification of discrete sites of hypersensitivity, or "hot spots", for LDE modification in the human proteome. Notably, most of these sites show clear preference for reacting with one of the three tested LDEs (HNE, 15d-PGJ2, 2-HD) and moderate, but not extreme levels of intrinsic reactivity. These findings, taken together, indicate that the potency of LDE-protein reactions in the proteome is dictated by a combination of molecular recognition and enhanced cysteine nucleophilicity.

Among the most LDE-sensitive cysteines, C22 of ZAK stood out as a particularly intriguing event, given the proposed role that this kinase plays in activating JNK, ERK, and p38 MAPK pathways in both cancer[35] and inflammation[36]. To date, only a handful of studies have investigated ZAK function and its modes of regulation remain poorly understood. Our findings identified ZAK as one of the highest potency targets of HNE in the human proteome. That HNE inhibits human ZAK by modifying an active site-proximal cysteine conserved among ZAK orthologues, but not other MAP3K enzymes, suggests ZAK acts as a special node in MAPK signaling pathways that confers sensitivity to lipid oxidation products. In this way, HNE modification of ZAK may limit the extent of JNK activation caused by oxidative stress, which could help certain cell types, such as tumor and immune cells, survive in the presence of high levels of reactive oxygen species. Further studies of ZAK function would benefit from the development of selective inhibitors for this enzyme. It is noteworthy, in this regard, that covalent inhibitors have recently been introduced for many kinases[24,45-47]. These inhibitors often target cysteine residues in or near kinase active sites, which leads us to speculate that the C22-HNE interaction discovered herein may offer a medicinal chemistry starting point for the development of ZAK inhibitors. Toward this end, competitive ABPP methods should offer a useful strategy to assess inhibitor target engagement and selectivity[48]. Beyond ZAK, we also identified several other kinases in our competitive isoTOP-ABPP experiments that possess cysteines that were inhibited by HNE, albeit with lower potencies. Prominent among these was cysteine (C311) in AKT1/2/3, which is an active site-proximal residue implicated in substrate-binding[49] and was inhibited by HNE with an IC50 value of 60 μM. These proteomic findings nicely confirm recent work showing that recombinant AKT2 is modified by HNE on C31125. Finally, we should emphasize that C22 in ZAK is just one of several hypersensitive sites for LDE modification identified in our competitive isoTOP-ABPP experiments (FIG. 2). We expect that more in-depth biological studies on these high-sensitivity targets of LDEs will reveal additional modes of crosstalk between oxidative stress and signaling pathways in mammalian cells.

From a methodological perspective, we believe that competitive isoTOP-ABPP offers several advantages over more conventional proteomic approaches for the discovery and characterization of protein-small molecule reactions in biological systems. First, quantitative inhibition values are measured in relative terms that are independent of absolute protein abundance. The method is therefore able to sift through signals that span a broad range of intensities to identify reactive sites that are more likely to bear functional consequence. Here, the site-specificity afforded by isoTOP-ABPP is important, since it permits the discovery of potent electrophile-cysteine reactions that may occur on proteins that display several lower-affinity cysteine-electrophile adducts (e.g., EEF2, FIG. 2*d*). Electrophiles also vary considerably in their structures and the stability of the protein adducts that they form. These features can complicate the direct detection of electrophile-protein interactions in proteomic studies.

Table 1, below, shows peptide sequences, parental protein names, and R values for IA-labeled cysteines that exhibit IA-labeling competed by one or more LDE with R values>5. HNE-competed cysteines are shaded in pink and 15d-PGJ2-competed cysteines are shaded in green. Note that REEP5 displays significant competition by both LDEs.

The isoTOP-ABPP method ABPP for quantitative mapping of cysteine-reactive, lipid-derived electrophile (LDE) reactions in proteomes, cells, tissues, or organisms can be used to determine if one or more proteins in the set of proteins therefrom possesses one or more domains, each comprising a reactive cysteine residue, has at least a low affinity (e.g., high micromolar affinity) for any selected structural module, and serves to identify what protein has that affinity. By combining a plurality of low-affinity structural modules having affinity for a particular protein binding site, a high affinity ligand for that protein can be constructed. Identification of a high affinity ligand can serve as a structural lead in the development of compounds targeting a particular protein, which can lead to the development of medicinal compounds. Similarly, identification of the protein target of the ligand can be of value in determining a possibly unknown function for the targeted protein.

TABLE 1

| IPI number | Name | Sequence | 4-HNE | PGJ2 | 2-HD |
|---|---|---|---|---|---|
| IPI00099986.5 | FN3KRP | ATGHSGGGC*ISQGR (SEQ ID NO: 3) | >15 | 1.62 | 1.03 |
| IPI00329638.10 | ZAK | FDDLQFFENC*GGGSFGSVYR (SEQ ID NO: 4) | >15 | 4.24 | 1.05 |
| IPI00021766.4 | RTN4 | YSNSALGHVNC*TIK (SEQ ID NO: 5) | 11.78 | 2.93 | 1.1 |
| IPI00186290.6 | EEF2 | STLTDSLVC*K (SEQ ID NO: 6) | 11.63 | 3.31 | 1.06 |
| IPI00141318.2 | CKAP4 | SSSSSSASAAAAAAAASSSASC*SR (SEQ ID NO: 7) | 7.73 | 3.33 | 1.08 |
| IPI00024670.5 | REEP5 | NC*MTDLLAK (SEQ ID NO: 8) | 7.08 | 7.38 | 1.18 |
| IPI00018235.3 | PEF1 | QALVNC*NWSSFNDETCLMMINMFDK (SEQ ID NO: 9) | 5.14 | 2.9 | 1.25 |
| IPI00024673.2 | MAPK9 | TLEEFQDVYLVMELMDANLC*QVIHMELDHER (SEQ ID NO: 10) | 5.08 | 1.78 | 1.14 |
| IPI00154451.6 | MMS19 | LMGLLSDPELGPAAADGFSLLMSDC*TDVLTR (SEQ ID NO: 11) | 1.78 | >15 | 1.1 |
| IPI00010158.3 | CHRAC1 | ATELFVQC*LATYSYR (SEQ ID NO: 12) | 1.94 | 12.32 | 1.06 |
| IPI00551062.2 | TNRC5 | QC*DVLVEEFEEVIEDWYR (SEQ ID NO: 13) | 1.29 | 11.77 | 1.06 |
| IPI00024254.3 | IFIT3 | GLNPLNAYSDLAEFLETEC*YQTPFNK (SEQ ID NO: 14) | 1.51 | 9.43 | 1.23 |
| IPI00639841.2 | PEC1 | WLSDEC*TNAVVNFLSR (SEQ ID NO: 15) | 1.86 | 8.23 | 1.06 |
| IPI00302925.3 | CCT8 | IAVYSC*PFDGMITETK (SEQ ID NO: 16) | 1.14 | 7.75 | 1.06 |
| IPI00155601.1 | MACROD1 | LEVDAIVNAANSSLLGGGGVDGC*IHR (SEQ ID NO: 17) | 1.56 | 7.65 | 1.02 |
| IPI00003814.1 | MAP2K6 | MC*DFGISGYLVDSVAK (SEQ ID NO: 18) | 1.9 | 7.43 | 1.15 |
| IPI00219103.6 | HPCA | LLQC*DPSSASQF (SEQ ID NO: 19) | 2.17 | 7.21 | 1.13 |
| IPI00793696.1 | RPL24 | C*ESAFLSK (SEQ ID NO: 20) | 1.74 | 6.78 | 1.25 |
| IPI00027223.2 | IDH1 | SEGGFIWAC*K (SEQ ID NO: 21) | 1.3 | 6.66 | 1.13 |
| IPI00021329.3 | WDR45L | C*NYLALVGGGK (SEQ ID NO: 22) | 3.34 | 6.45 | 1.06 |
| IPI00640155.1 | PSMB8 | LLSNMMC*QYR (SEQ ID NO: 23) | 1.19 | 5.86 | 1.05 |

TABLE 1-continued

| IPI number | Name | Sequence | 4-HNE | PGJ2 | 2-HD |
|---|---|---|---|---|---|
| IPI00022431.1 | AHSG | C*DSSPDSAEDVR (SEQ ID NO: 24) | 1.35 | 5.73 | 1.12 |
| IPI00007675.6 | DYNC1L11 | VGSFGSSPPGLSSTYTGGPLGNEIASGNGGAAAGDDEDGQNLWSC*ILSEVSTR (SEQ ID NO: 25) | 2.59 | 5.18 | 1.1 |
| IPI00010153.5 | RPL23 | ISLGLPVGAVINC*ADNTGAK (SEQ ID NO: 26) | 1.73 | 5.06 | 1.87 |

EXAMPLES

Preparation of Human Cancer Cell Line Proteomes

MDA-MB-231 cells were grown in L15 media supplemented with 10% fetal bovine serum at 37° C. in a $CO_2$-free incubator. For in vitro labeling experiments, cells were grown to 100% confluency, washed three times with PBS and scraped in cold PBS. Cell pellets were isolated by centrifugation at 1400×g for 3 min, and the cell pellets stored at −80° C. until further use. The harvested cell pellets were lysed by sonication in PBS buffer and fractionated by centrifugation (100,000×g, 45 min.) to yield soluble and membrane proteomes. The proteomes were prepared fresh from the frozen cell pallets prior to each experiment.

In Vitro LDE Treatment

HNE was purchased from EMD biosciences, 15d-PGJ2 was purchased from Cayman Chemicals and 2-HD was purchased from Santa Cruz Biotechnology. Proteome samples were diluted to a 4 mg protein/mL solution in PBS. For each profiling experiment, one aliquot of the proteome sample (0.5 mL) was treated with 100 µM of LDE using 5 µL of a 10 mM stock and the other aliquot was treated with 5 µL of either ethanol (for HNE and 15d-PGJ2) or DMSO (for 2-HD) as control. For the concentration-dependent profiling experiments using HNE, aliquots of the proteomes (0.5 mL each) were treated with 5, 10, 50, 100 and 500 µM of HNE using 5 µL of 0.5, 1.0, 5, 10 and 50 mM of stock solution, respectively. After 60 minutes of treatment at room temperature, both the LDE-treated and control aliquots were passed through a NAP-5 Sephadex column (GE healthcare) to remove any unreacted LDE. The volume of each aliquot was increased to 1 mL with the concentration at 2 mg/mL after this step.

In Situ HNE Treatment

After MDA-MB-231 cells were grown to 100% confluency, the media was removed and replaced with fresh serum-free media containing 100 µM HNE (20 µL of 50 mM stock in 10 mL media). A control flask of cells was treated with 10 mL of serum-free media containing 20 uL of ethanol in parallel. The cells were incubated at 37° C. for 1 hour and harvested as detailed above to prepare HNE-treated and control proteomes, respectively.

Protein Labeling and Click Chemistry

Each of the control and LDE-treated proteome samples (~2 mg protein/mL in 1 mL volume) was treated with 100 µM of IA-probe using 10 µL of a 10 mM stock in DMSO. The labeling reactions were incubated at room temperature for 1 hour. Click chemistry (acetylene-azide cycloaddition) was performed by the addition of 100 µM of either the Heavy-TEV-Tag (for the control sample) or Light-TEV-Tag (for the LDE-treated sample) (20 µL of a 5 mM stock), 1 mM TCEP (fresh 50× stock in water), 100 µM ligand (17× stock in DMSO:t-Butanol 1:4) and 1 mM $CuSO_4$ (50× stock in water). Samples were allowed to react at room temperature for 1 hour. After the click chemistry step, the light and heavy-labeled samples were mixed together and centrifuged (5900×g, 4 min, 4° C.) to pellet the precipitated proteins.

The pellets were washed twice in cold MeOH, after which the pellet was solubilized in PBS containing 1.2% SDS via sonication and heating (5 min, 80° C.). Samples were subjected to streptavidin enrichment of probe-labeled proteins, sequential on-bead trypsin and TEV digestion, and liquid chromatography-mass spectrometry (LC-MS) analysis according to the published isoTOP-ABPP protocol[30].

MS Data Analysis

IA-probe labeled peptides were identified by SEQUEST2 and DTASelect3, and the quantification of heavy/light ratios (isoTOP-ABPP ratios, R) was performed by an in-house software (CIMAGE) as previously described. The software was advanced to be able to detect and quantify cases where near complete LDE blockade of IA-probe labeling was achieved (e.g., very small or no light peak) and assign an empirical ratio cut-off of 15 to each of such cases. Each experiment consisted of multiple LC/LCMS/MS runs: either FINE, 15d-PGJ2 and 2-HD 100 µM competition, or HNE competition at different concentrations. All runs were searched using SEQUEST and filtered with DTASelect as described above. Because the mass-spectrometer was configured for data-dependant fragmentation, peptides are not always identified in every run. In the case of probe-modified peptides that were sequenced in one, but not the other runs, a featured algorithm of CIMAGE was utilized to identify the corresponding peak pairs in the runs without the SEQUEST identification and obtain quantification as previously described. In all cases, the false-positive rate after quantification was found to be less than 1%.

After ratios for unique peptide entries are calculated for each experiment, overlapping peptides with the same labeled cysteine (e.g., same local sequence around the labeled cysteines but different charge states, MudPIT segment numbers, or tryptic termini) are grouped together, and the median ratio from each group is reported as the final ratio ("R").

Retroviral Overexpression of FLAG-Tagged ZAK Proteins in HEK-293T Cells

Full-length cDNA encoding human ZAK-13 (BC001401) in pOTB7 was purchased from Open BioSystems and subcloned into pFLAG-CMV-6c (Sigma-Aldrich). ZAK-C22A and ZAK-K45M mutants were generated by QuikChange site-directed mutagenesis using the primer 5'-atttgatgactt-gcagttttttgaaaacgccggtggaggaagttttg-3' (SEQ ID NO:1) and 5'-ggacaaggaggtggctgtaatgaagctcctcaaaatagag-3' (SEQ ID NO:2) and their complements. Wild-type and mutant ZAK were cloned into a modified pCLNCX retroviral vector. Retrovirus was prepared by taking 3.0 µg of each of pCLNCX and pCL-Ampho vectors and 18 4, of FuGENE IID reagent (Roche) to transfect 60% confluent HEK-293T cells. Medium was replaced after 1 day of transfection and on the next day virus-containing supernatant was collected, filter sterilized and stored at −70° C. 1 mL of virus-containing medium was used to infect target cells in presence of 8 μg/mL of polybrene for 72 hours and infected cells were selected in medium containing 100 μg/mL of hygromycin. Surviving cells after the selection were expanded and cultured in regular DMEM medium with 10% FCS.

Immunoprecipitation of FLAG-Tagged ZAK Proteins

HEK-293T cells with stable expression of wild-type or mutant ZAK were grown to 100% confluency on a 10 cm plate. Cells were collected, washed with cold PBS (2×10 mL) and lysed in 1 mL of PBS supplemented with 1× complete EDTA-free protease inhibitor cocktails by sonication. Cell lysates were fractionated by centrifugation (100,000×g, 45 min) and the soluble fraction was incubated with 504, of Anti-FLAG M2 affinity gel (Sigma-Aldrich) at 4° C. for 3 hours. Beads were washed with 5×1 mL of cold PBS (10 min per incubation) and FLAG-ZAK were eluted by either 150 μg/mL of FLAG-peptide solution provided by manufacturer or by 4× gel loading buffer depending on the downstream applications.

In-Gel Fluorescence Characterization of ZAK Labeled by IA Probe

FLAG-tagged wild-type and C22A mutant ZAK were immunoprecipitated from HEK-293T cells (1×107). After washing with PBS, the beads were suspended in 100 μL of PBS buffer and labeled with 250 nM of IA-rhodamine (add 1 μL of 25 μM probe stock in DMSO). After 1 hour of labeling at 4° C., 50 μL of 4× gel loading buffer was added and the beads were boiled for 5 min to elute the bound proteins. Gel samples were separated by SDS-PAGE (50 μL of sample/lane) and visualized in-gel using a Hitachi FMBio II flatbed laser-induced fluorescence scanner (MiraiBio, Alameda, Calif.). For testing HNE blockade on IA labeling of ZAK by gel, soluble lysate of HEK-293T overexpressing WT-ZAK were incubated with 10, 50 and 100 μM of FINE (add 2 μL of 5, 25 and 50 mM stock) for 30 mins and then subjected to immunoprecipitation.

In-Gel Fluorescence Characterization of ZAK Labeled by HNEyne Probe

50 μL of soluble lysate (1 mg/mL in PBS) of HEK-239T cells transfected with mock ZAKWT and ZAK-C22A was labeled with 10 μM of HNEyne4 (Cayman Chemicals, 1 μL of 500 μM stock in ethanol) for 1 hour at room temperature. Cycloaddition was performed with 200 μM rhodamine-azide, 1 mM TCEP, 100 μM TBTA ligand and 1 mM $CuSO_4$. The reaction was allowed to proceed at room temperature for 1 hour before quenching with 20 μL of 4×SDS-PAGE loading buffer (reducing). Quenched reactions were separated by SDS-PAGE (40 μL of sample/lane) and visualized in-gel using a fluorescence scanner. For the in situ HNEyne labeling, WT- and C22A-ZAK transfected cells were grown in a 6-well plate to 100% confluency and switched into 1 mL of serum-free DMEM medium. Cells were labeled with 5 μM of HNEyne probe (1 μL of 5 mM stock) for 1 hour at 37° C. Cells were then harvested, washed with cold PBS and lysed in 200 μL of PBS with protease inhibitors. 50 μL of soluble lysates were subjected to the cycloaddition protocol as described above and probe labeling was monitored by in-gel fluorescence.

ZAK In Vitro Kinase Activity Assay

The kinase activity assay protocol was adapted from Yu et al[5]. Kinase assay buffers, Myeilin Basic Protein (MBP) substrate, and ATP stock solution were purchased from SignalChem. Radio-labeled [$^{33}$P]-ATP was purchased from PerkinElmer. 10 mg of soluble lysate of HEK-293T cells transfected with each of wild-type, C22A and K45M of ZAK were immunoprecipitated and then eluted with 2×300 μL FLAG-peptide buffer. Each sample was concentrated to 100 μL using an Amicon centrifugal filter (30 kDa cutoff) and exchanged to the assay kinase buffer (5 mM MOPS, pH7.2, 2.5 mM β-glycerol-phosphate, 5 mM MgCl2, 1 mM EGTA, 0.4 mM EDTA, 0.05 mM DTT and 40 ng/μL BSA) to a final volume around 10 μL. For each ZAK construct, 4 reactions were set up and each reaction starts with mixing 10 μL of immunoprecipitated ZAK, 5 μL of MBP (1 mg/mL) and 5 μL of HNE (10 or 100 μM) or $H_2O$ together. No-enzyme and no-substrate controls were prepared in parallel. The mixed samples were incubated on ice for 15 min and 5 μL of [$^{33}$P]-ATP assay cocktail (250 μM, 167 μCi/mL) was then added to initiate the kinase reaction. Each reaction mixture was incubated in 30° C. for 15 min and the reaction was terminated by spotting 20 μL of the reaction mixture onto individual pre-cut strips of phosphocellulose P81 paper. The spotted P81 strips were air dried and then washed with 10 mL of 1% phosphoric acid for 3×10 min ZAK activity was measured by counting the radioactivity on the P81 paper in the presence of scintillation fluid in a scintillation counter after subtracting the value obtained from the corresponding no substrate control, and was normalized to that of ZAK-WT without HNE treatment. Experiments were performed in triplicates. 10 μL of each ZAK variant used in setting up the kinase reaction were run on a SDS-PAGE gel and immunoblotted with an anti-FLAG antibody to ensure that they are enriched at similar levels.

Measurement of HNE Blockade of ATP Binding of ZAK by SILAC-ABPP

HEK-293T cells with stable expression of wild-type ZAK were passaged six times in DMEM medium minus 1-lysine and 1-arginine (Thermo) supplemented 10% dialyzed FBS (Gemini), 1% PSQ (1% vol/vol 10,000 units penicillin, 10 mg streptomycin, 29.2 mg lglutamate solution) and 100 μg/mL [$^{13}C_6$, $^{15}N_4$] 1-arginineHCl and [$^{13}C_6$,$^{15}N_2$] 1-lysine-HCl (heavy) or 1-arginineHCl and 1-lysineHCl (light) (Sigma-Aldrich). Soluble proteomes of light and heavy ZAK-WT transfected HEK-293T cells (3 mL each at 7 mg/mL) were treated with 100 μM of HNE (6 μL of 50 mM stock) or EtOH for 30 min at room temperature. The samples were gel filtrated by PD-10 columns (GE healthcare) to remove unreacted HNE as well as excessive ATP molecules in proteomes. Each aliquot of light and heavy proteomes (0.5 mL, 6 mg/mL) was labeled with 20 μM of acylphosphate-ATP probe (ActivX Biosciences) and then mixed together to proceed with reduction/alkylation, streptavidin enrichment, trypsin digest according to a modified version of the vendor-provided "Xsite Kinase Analysis" protocol6. The trypsin digested samples were analysed by LC-MS/MS and enriched kinase peptides were identified by SEQUEST and DTASelect. The amounts of probe-labeled kinases with and without HNE treatment were quantified using the CIMAGE module that was developed for quantitative SILAC-ABPP chemoproteomic profiling. As internal controls, light and heavy proteomes were trypsin digested without probe labeling and streptavidin enrichment, and analysed by LC-MS/MS to quantify the basic level of each kinase between light and heavy samples. The normalized ratio, for each identified kinase, was computed by dividing the ratio from the probe-labeling experiment by that from the unenriched experiment, and these ratios (from four replicates) were used to calculate the means and standard deviations that were reported in FIG. 4*e*.

Western Blotting of Phospho-MAPKs in ZAK-Transfected HEK-293T Cells.

Mouse and rabbit monoclonal antibodies against phospho-ERK 1/2 (Thr202/Tyr204), phosphor-SAPK/JNK (Thr183/Thr185), phosphor-p38 MAPK (Thr180/Thr182) and total ERK 1/2, SAPK/JNK and p38 MAPK were purchased from Cell Signaling Technology. HEK-293T cells transfected with mock, WT-ZAK, C22A-ZAK and K45M-ZAK were seeded into a 12-well plate with $2.5\times10^5$ cells per well. Cells were grown in regular DMEM medium with 10% FBS for 24 hours and starved in serum-free DMEM medium for another 24 hours. Cells were then treated at 37° C. either with 100 μM of HNE (2 μL of 50 mM stock) for 30 min followed by 1 mM of $H_2O_2$ for 30 min, or with 50 and 100 μM of HNE alone for 60 min After the treatment, cells were harvested, washed with 2×1 mL of cold PBS, and then lysed by sonication in 1004, of PBS buffer supplemented with 1× complete protease inhibitors cocktail and 1×PhosSTOP phosphatase inhibitors cocktail (Roche). 30 μg of soluble lysate of each sample was separated by SDS-PAGE, transferred to nitrocellulose membrane, blocked in 5% milk TBST and blotted against the primary antibodies (1:2000) listed above for 16 hours at 4° C. After washing in TBST (3×10 minutes), membranes were blotted with IRDye secondary antibodies (1:10,000) for 1 hour at room temperature and scanned by an Odyssey imaging system (LI-COR). Protein band intensities were quantified by ImageJ8 and ratios of phosphor-MAPK over total MAPK were computed. Experiments were repeated in at least four replicates.

DOCUMENTS CITED

1. Walsh, C. T. *Posttranslational Modification of Proteins. Expanding Nature's Inventory*., (Roberts & Company, Greenwood Village, C O, 2005).
2. Leitner, A. & Lindner, W. Chemistry meets *proteomics*: the use of chemical tagging reactions for MS-based proteomics. *Proteomics* 6, 5418-34 (2006).
3. Tate, E. W. Recent advances in chemical proteomics: exploring the posttranslational proteome. *J Chem Biol* 1, 17-26 (2008).
4. Hang, H. C. & Linder, M. E. Exploring protein lipidation with chemical biology. *Chem Rev* 111, 6341-58 (2011).
5. Jacobs, A. T. & Marnett, L. J. Systems analysis of protein modification and cellular responses induced by electrophile stress. *Acc Chem Res* 43, 673-83 (2010).
6. Leonard, S. E. & Carroll, K. S. Chemical 'omics' approaches for understanding protein cysteine oxidation in biology. *Curr Opin Chem Biol* 15, 88-102 (2011).
7. Gueraud, F., Atalay, M., Bresgen, N., Cipak, A., Eckl, P. M., Huc, L., Jouanin, I., Siems, W. & Uchida, K. Chemistry and biochemistry of lipid peroxidation products. *Free Radic Res* 44, 1098-124 (2010).
8. Dubinina, E. E. & Dadali, V. A. Role of 4-hydroxy-trans-2-nonenal in cell functions. *Biochemistry* (*Mosc*) 75, 1069-87 (2010).
9. Fritz, K. S. & Petersen, D. R. An overview of the chemistry and biology of reactive aldehydes. *Free Radic Biol Med* (2012).
10. Rudolph, T. K. & Freeman, B. A. Transduction of redox signaling by electrophile-protein reactions. *Sci Signal* 2, re7 (2009).
11. Fritz, K. S. & Petersen, D. R. Exploring the biology of lipid peroxidation-derived protein carbonylation. *Chem Res Toxicol* 24, 1411-9 (2011).
12. Leonarduzzi, G., Robbesyn, F. & Poli, G. Signaling kinases modulated by 4-hydroxynonenal. *Free Radic Biol Med* 37, 1694-702 (2004).
13. Jacobs, A. T. & Marnett, L. J. Heat shock factor 1 attenuates 4-Hydroxynonenal mediated apoptosis: critical role for heat shock protein 70 induction and stabilization of Bcl-XL. *J Biol Chem* 282, 33412-20 (2007).
14. Surh, Y. J., Na, H. K., Park, J. M., Lee, H. N., Kim, W., Yoon, I. S. & Kim, D. D. 15-Deoxy-Delta(1)(2),(1)(4)-prostaglandin J(2), an electrophilic lipid mediator of antiinflammatory and pro-resolving signaling. *Biochem Pharmacol* 82, 1335-51 (2011).
15. Chipuk, J. E., McStay, G. P., Bharti, A., Kuwana, T., Clarke, C. J., Siskind, L. J., Obeid, L. M. & Green, D. R. Sphingolipid metabolism cooperates with BAK and BAX to promote the mitochondrial pathway of apoptosis. *Cell* 148, 988-1000 (2012).
16. Vila, A., Tallman, K. A., Jacobs, A. T., Liebler, D. C., Porter, N. A. & Marnett, L. J. Identification of protein targets of 4-hydroxynonenal using click chemistry for ex vivo biotinylation of azido and alkynyl derivatives. *Chem Res Toxicol* 21, 432-44 (2008).
17. Codreanu, S. G., Zhang, B., Sobecki, S. M., Billheimer, D. D. & Liebler, D. C. Global analysis of protein damage by the lipid electrophile 4-hydroxy-2-nonenal. *Mol Cell Proteomics* 8, 670-80 (2009).
18. Han, B., Hare, M., Wickramasekara, S., Fang, Y. & Maier, C. S. A comparative 'bottom up' proteomics strategy for the site-specific identification and quantification of protein modifications by electrophilic lipids. *J Proteomics* 75, 5724-33 (2012).
19. Roe, M. R., Xie, H., Bandhakavi, S. & Griffin, T. J. Proteomic mapping of 4-hydroxynonenal protein modification sites by solid-phase hydrazide chemistry and mass spectrometry. *Anal Chem* 79, 3747-56 (2007).
20. Kim, H. Y., Tallman, K. A., Liebler, D. C. & Porter, N. A. An azido-biotin reagent for use in the isolation of protein adducts of lipid-derived electrophiles by streptavidin catch and photorelease. *Mol Cell Proteomics* 8, 2080-9 (2009).
21. Perluigi, M., Coccia, R. & Butterfield, D. A. 4-Hydroxy-2-nonenal, a reactive product of lipid peroxidation, and neurodegenerative diseases: a toxic combination illuminated by redox proteomics studies. *Antioxid Redox Signal* 17, 1590-609 (2012).
22. Aldini, G., Carini, M., Vistoli, G., Shibata, T., Kusano, Y., Gamberoni, L., Dalle-Donne, I., Milzani, A. & Uchida, K. Identification of actin as a 15-deoxy-Delta12,14-prostaglandin J2 target in neuroblastoma cells: mass spectrometric, computational, and functional approaches to investigate the effect on cytoskeletal derangement. *Biochemistry* 46, 2707-18 (2007).
23. Singh, J., Petter, R. C., Baillie, T. A. & Whitty, A. The resurgence of covalent drugs. *Nat Rev Drug Discov* 10, 307-17 (2011).
24. Liu, Q., Sabnis, Y., Zhao, Z., Zhang, T., Buhrlage, S. J., Jones, L. H. & Gray, N. S. Developing irreversible inhibitors of the protein kinase cysteinome. *Chem Biol* 20, 146-59 (2013).
25. Shearn, C. T., Fritz, K. S., Reigan, P. & Petersen, D. R. Modification of Akt2 by 4-hydroxynonenal inhibits insulin-dependent Akt signaling in HepG2 cells. *Biochemistry* 50, 3984-96 (2011).
26. Bennaars-Eiden, A., Higgins, L., Hertzel, A. V., Kapphahn, R. J., Ferrington, D. A. & Bernlohr, D. A. Covalent modification of epithelial fatty acid-binding protein by 4-hydroxynonenal in vitro and in vivo. Evidence for a role in antioxidant biology. *J Biol Chem* 277, 50693-702 (2002).
27. Higdon, A. N., Dranka, B. P., Hill, B. G., Oh, J. Y., Johnson, M. S., Landar, A. & Darley-Usmar, V. M. Methods for imaging and detecting modification of proteins by reactive lipid species. *Free Radic Biol Med* 47, 201-12 (2009).

28. LoPachin, R. M., Gavin, T., Petersen, D. R. & Barber, D. S. Molecular mechanisms of 4-hydroxy-2-nonenal and acrolein toxicity: nucleophilic targets and adduct formation. *Chem Res Toxicol* 22, 1499-508 (2009).

29. Doom, J. A. & Petersen, D. R. Covalent modification of amino acid nucleophiles by the lipid peroxidation products 4-hydroxy-2-nonenal and 4-oxo-2-nonenal. *Chem Res Toxicol* 15, 1445-50 (2002).

30. Weerapana, E., Wang, C., Simon, G. M., Richter, F., Khare, S., Dillon, M. B., Bachovchin, D. A., Mowen, K., Baker, D. & Cravatt, B. F. Quantitative reactivity profiling predicts functional cysteines in proteomes. *Nature* 468, 790-5 (2010).

31. Rostovtsev, V. V., Green, J. G., Fokin, V. V. & Sharpless, K. B. A stepwise Huisgen cycloaddition process: copper (I)-catalyzed regioselective "ligation" of azides and terminal alkynes. *Angew. Chem. Int. Ed. Engl.* 41, 2596-2599 (2002).

32. Bloem, L. J., Pickard, T. R., Acton, S., Donoghue, M., Beavis, R. C., Knierman, M. D. & Wang, X. Tissue distribution and functional expression of a cDNA encoding a novel mixed lineage kinase. *J Mol Cell Cardiol* 33, 1739-50 (2001).

33. Gotoh, I., Adachi, M. & Nishida, E. Identification and characterization of a novel MAP kinase kinase kinase, MLTK. *J Biol Chem* 276, 4276-86 (2001).

34. Keshet, Y. & Seger, R. The MAP kinase signaling cascades: a system of hundreds of components regulates a diverse array of physiological functions. *Methods Mol Biol* 661, 3-38 (2010).

35. Yang, J. J., Lee, Y. J., Hung, H. H., Tseng, W. P., Tu, C. C., Lee, H. & Wu, W. J. ZAK inhibits human lung cancer cell growth via ERK and JNK activation in an AP-1-dependent manner. *Cancer Sci* 101, 1374-81 (2010).

36. Wong, J., Smith, L. B., Magun, E. A., Engstrom, T., Kelley-Howard, K., Jandhyala, D. M., Thorpe, C. M., Magun, B. E. & Wood, L. J. Small molecule kinase inhibitors block the ZAK-dependent inflammatory effects of doxorubicin. *Cancer Biol Ther* 14, 56-63 (2013).

37. Wang, X., Mader, M. M., Toth, J. E., Yu, X., Jin, N., Campbell, R. M., Smallwood, J. K., Christe, M. E., Chatterjee, A., Goodson, T., Jr., Vlahos, C. J., Matter, W. F. & Bloem, L. J. Complete inhibition of anisomycin and UV radiation but not cytokine induced JNK and p38 activation by an aryl-substituted dihydropyrrolopyrazole quinoline and mixed lineage kinase 7 small interfering RNA. *J Biol Chem* 280, 19298-305 (2005).

38. Yu, X. & Bloem, L. J. Effect of C-terminal truncations on MLK7 catalytic activity and JNK activation. *Biochem Biophys Res Commun* 310, 452-7 (2003).

39. Bachovchin, D. A., Mohr, J. T., Speers, A. E., Wang, C., Berlin, J. M., Spicer, T. P., Fernandez-Vega, V., Chase, P., Hodder, P. S., Schurer, S. C., Nomura, D. K., Rosen, H., Fu, G. C. & Cravatt, B. F. Academic cross-fertilization by public screening yields a remarkable class of protein phosphatase methylesterase-1 inhibitors. *Proc Nati Acad Sci USA* 108, 6811-6 (2011).

40. Patricelli, M. P., Szardenings, A. K., Liyanage, M., Nomanbhoy, T. K., Wu, M., Weissig, H., Aban, A., Chun, D., Tanner, S. & Kozarich, J. W. Functional interrogation of the kinome using nucleotide acyl phosphates. *Biochemistry* 46, 350-8 (2007).

41. Shen, H. M. & Liu, Z. G. JNK signaling pathway is a key modulator in cell death mediated by reactive oxygen and nitrogen species. *Free Radic Biol Med* 40, 928-39 (2006).

42. Forman, H. J. Reactive oxygen species and alpha,beta-unsaturated aldehydes as second messengers in signal transduction. *Ann N Y Acad Sci* 1203, 35-44 (2010).

43. Kutuk, O. & Basaga, H. Apoptosis signalling by 4-hydroxynonenal: a role for JNK-c-Jun/AP-1 pathway. Redox Rep 12, 30-4 (2007).

44. Uchida, K. 4-Hydroxy-2-nonenal: a product and mediator of oxidative stress. *Prog Lipid Res* 42, 318-43 (2003).

45. Gushwa, N. N., Kang, S., Chen, J. & Taunton, J. Selective targeting of distinct active site nucleophiles by irreversible SRC-family kinase inhibitors. *J Am Chem Soc* 134, 20214-7 (2012).

46. Cohen, M. S., Zhang, C., Shokat, K. M. & Taunton, J. Structural bioinformatics based design of selective, irreversible kinase inhibitors. *Science* 308, 1318-21 (2005).

47. Zhou, W., Hur, W., McDermott, U., Dutt, A., Xian, W., Ficarro, S. B., Zhang, J., Sharma, S. V., Brugge, J., Meyerson, M., Settleman, J. & Gray, N. S. A structure 16 guided approach to creating covalent FGFR inhibitors. *Chem Biol* 17, 285-95 (2010).

48. Simon, G. M., Niphakis, M. J. & Cravatt, B. F. Determining target engagement in living systems. *Nat Chem Biol* 9, 200-5 (2013).

49. Huang, X., Begley, M., Morgenstern, K. A., Gu, Y., Rose, P., Zhao, H. & Zhu, X. Crystal structure of an inactive Akt2 kinase domain. *Structure* 11, 21-30 (2003).

50. Carbone, D. L., Doom, J. A., Kiebler, Z., Ickes, B. R. & Petersen, D. R. Modification of heat shock protein 90 by 4-hydroxynonenal in a rat model of chronic alcoholic liver disease. *J Pharmacol Exp Ther* 315, 8-15 (2005).

51. Carbone, D. L., Doom, J. A., Kiebler, Z., Sampey, B. P. & Petersen, D. R. Inhibition of Hsp72-mediated protein refolding by 4-hydroxy-2-nonenal. *Chem Res Toxicol* 17, 1459-67 (2004).

52. Deng, X., Weerapana, E., Ulanovskaya, O., Sun, F., Liang, H., Ji, Q., Ye, Y., Fu, Y., Zhou, L., Li, J., Zhang, H., Wang, C., Alvarez, S., Hicks, L. M., Lan, L., Wu, M., Cravatt, B. F. & He, C. Proteome-wide Quantification and Characterization of Oxidation-Sensitive Cysteines in Pathogenic Bacteria. *Cell Host Microbe* 13, 358-70 (2013).

53. Wang, T., Kartika, R. & Spiegel, D. A. Exploring post-translational arginine modification using chemically synthesized methylglyoxal hydroimidazolones. *J Am Chem Soc* 134, 8958-67 (2012).

54. Weerapana, E., Simon, G. M. & Cravatt, B. F. Disparate proteome reactivity profiles of carbon electrophiles. *Nat Chem Biol* 4, 405-7 (2008).

55. Ban, H., Gavrilyuk, J. & Barbas, C. F., 3rd. Tyrosine bioconjugation through aqueous ene-type reactions: a click-like reaction for tyrosine. *J Am Chem Soc* 132, 1523-5 (2010).

56. Fujishima, S. H., Yasui, R., Mild, T., Ojida, A. & Hamachi, I. Ligand-directed acyl imidazole chemistry for labeling of membrane-bound proteins on live cells. *J Am Chem Soc* 134, 3961-4 (2012).

57. Parola, M., Robino, G., Marra, F., Pinzani, M., Bellomo, G., Leonarduzzi, G., Chiarugi, P., Camandola, S., Poli, G., Waeg, G., Gentilini, P. & Dianzani, M. U. HNE interacts directly with JNK isoforms in human hepatic stellate cells. *J Clin Invest* 102, 1942-50 (1998).

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of screening one or more selective modulators of a kinase protein target, comprising:

(a) contacting a first set of proteins of a mammalian cell with a lipid-derived electrophile, wherein the lipid-derived electrophile is cysteine-reactive, lipid-derived electrophile that is a Michael acceptor having an α,β-unsaturated carbonyl group to generate an alkylated set of proteins;

(b) contacting the alkylated set of proteins with an alkynylated iodoacetamide probe, followed by reaction with an azido compound comprising a first isotopic marker, to provide an isotopically-marked alkylated set of proteins, wherein the reaction with the azido compound is carried out using a copper- catalyzed azide-alkyne cycloaddition reaction;

(c) contacting the first set of proteins of a mammalian cell of step (a), not exposed to the lipid- derived electrophile, with an alkynylated iodoacetamide probe, followed by reaction with an azido compound comprising a second isotopic marker, to provide an isotopically-marked control set of proteins, wherein the reaction with the azido compound is carried out using a copper-catalyzed azide-alkyne cycloaddition reaction, and wherein the first isotopic marker and the second isotopic marker are isotopically-differentiated azide-biotin tags comprising a Tobacco Etch Virus (TEV) cleavage sequence;

(d) combining the isotopically-marked alkylated set of proteins and the isotopically-marked control set of proteins to provide a combined sample;

(e) quantifying reactivities of the isotopically-marked alkylated set of proteins and the isotopically-marked control set of proteins to identify a kinase protein target by comparing the abundance of the first isotopic marker and the abundance of the second isotopic marker for each protein of the combined sample, wherein the kinase protein target possess at least 5-fold or higher ratio of the second isotopic marker to the first isotopic marker among the proteins of the combined sample, and wherein the site of selective cysteine modification by a lipid-derived electrophile is at a non-active site;

(f) incubating the kinase protein target with a plurality of candidate compounds to detect a binding between a candidate compound and the kinase protein target; and (g) identifying one or more selective modulators of the kinase protein target, wherein the lipid-derived electrophile and the alkynylated iodoacetamide probe each independently has a micromolar affinity to the isotopically-marked alkylated set of proteins of a mammalian cell and to the isotopically-marked control set of proteins of a control mammalian cell.

2. The method of claim 1, wherein the first set of proteins includes two or more proteins.

3. The method of claim 1, wherein the lipid-derived electrophile is a stress-induced electrophile.

4. The method of claim 1, wherein the lipid-derived electrophile undergoes a Michael conjugate addition reaction with a cysteine residue of one or more proteins of the first set of proteins.

5. The method of claim 4, wherein the lipid-derived electrophile is 4-hydroxynonenal (HNE) or 15-deoxy-Al 2,14-prostaglandin J2 (15d-PGJ2).

6. The method of claim 1, wherein the one or more selective modulators of the kinase protein target is a reversible inhibitor of the kinase protein target.

* * * * *

SEQUENCE LISTING

```
<160> NUMBER OF SEQ ID NOS: 46

<210> SEQ ID NO 1
<211> LENGTH: 47
<212> TYPE: DNA
<213> ORGANISM: Artificial Sequence
<220> FEATURE:
<223> OTHER INFORMATION: A synthetic primer

<400> SEQUENCE: 1

atttgatgac ttgcagtttt ttgaaaacgc cggtggagga agttttg                   47


<210> SEQ ID NO 2
<211> LENGTH: 40
<212> TYPE: DNA
<213> ORGANISM: Artificial Sequence
<220> FEATURE:
<223> OTHER INFORMATION: A synthetic primer

<400> SEQUENCE: 2

ggacaaggag gtggctgtaa tgaagctcct caaaatagag                           40


<210> SEQ ID NO 3
<211> LENGTH: 14
<212> TYPE: PRT
<213> ORGANISM: Homo sapiens

<400> SEQUENCE: 3

Ala Thr Gly His Ser Gly Gly Gly Cys Ile Ser Gln Gly Arg
1               5                   10


<210> SEQ ID NO 4
<211> LENGTH: 20
<212> TYPE: PRT
<213> ORGANISM: Homo sapiens

<400> SEQUENCE: 4

Phe Asp Asp Leu Gln Phe Phe Glu Asn Cys Gly Gly Gly Ser Phe Gly
1               5                   10                  15

Ser Val Tyr Arg
            20


<210> SEQ ID NO 5
<211> LENGTH: 14
<212> TYPE: PRT
<213> ORGANISM: Homo sapiens

<400> SEQUENCE: 5

Tyr Ser Asn Ser Ala Leu Gly His Val Asn Cys Thr Ile Lys
1               5                   10


<210> SEQ ID NO 6
<211> LENGTH: 10
<212> TYPE: PRT
<213> ORGANISM: Homo sapiens

<400> SEQUENCE: 6

Ser Thr Leu Thr Asp Ser Leu Val Cys Lys
1               5                   10
```

-continued

<210> SEQ ID NO 7
<211> LENGTH: 24
<212> TYPE: PRT
<213> ORGANISM: Homo sapiens

<400> SEQUENCE: 7

```
Ser Ser Ser Ser Ser Ser Ala Ser Ala Ala Ala Ala Ala Ala Ala Ala
1               5                   10                  15

Ser Ser Ser Ala Ser Cys Ser Arg
            20
```

<210> SEQ ID NO 8
<211> LENGTH: 9
<212> TYPE: PRT
<213> ORGANISM: Homo sapiens

<400> SEQUENCE: 8

```
Asn Cys Met Thr Asp Leu Leu Ala Lys
1               5
```

<210> SEQ ID NO 9
<211> LENGTH: 25
<212> TYPE: PRT
<213> ORGANISM: Homo sapiens

<400> SEQUENCE: 9

```
Gln Ala Leu Val Asn Cys Asn Trp Ser Ser Phe Asn Asp Glu Thr Cys
1               5                   10                  15

Leu Met Met Ile Asn Met Phe Asp Lys
            20                  25
```

<210> SEQ ID NO 10
<211> LENGTH: 31
<212> TYPE: PRT
<213> ORGANISM: Homo sapiens

<400> SEQUENCE: 10

```
Thr Leu Glu Glu Phe Gln Asp Val Tyr Leu Val Met Glu Leu Met Asp
1               5                   10                  15

Ala Asn Leu Cys Gln Val Ile His Met Glu Leu Asp His Glu Arg
            20                  25                  30
```

<210> SEQ ID NO 11
<211> LENGTH: 31
<212> TYPE: PRT
<213> ORGANISM: Homo sapiens

<400> SEQUENCE: 11

```
Leu Met Gly Leu Leu Ser Asp Pro Glu Leu Gly Pro Ala Ala Ala Asp
1               5                   10                  15

Gly Phe Ser Leu Leu Met Ser Asp Cys Thr Asp Val Leu Thr Arg
            20                  25                  30
```

<210> SEQ ID NO 12
<211> LENGTH: 15
<212> TYPE: PRT
<213> ORGANISM: Homo sapiens

<400> SEQUENCE: 12

```
Ala Thr Glu Leu Phe Val Gln Cys Leu Ala Thr Tyr Ser Tyr Arg
1               5                   10                  15
```

-continued

<210> SEQ ID NO 13
<211> LENGTH: 18
<212> TYPE: PRT
<213> ORGANISM: Homo sapiens

<400> SEQUENCE: 13

```
Gln Cys Asp Val Leu Val Glu Glu Phe Glu Glu Val Ile Glu Asp Trp
1               5                   10                  15

Tyr Arg
```

<210> SEQ ID NO 14
<211> LENGTH: 26
<212> TYPE: PRT
<213> ORGANISM: Homo sapiens

<400> SEQUENCE: 14

```
Gly Leu Asn Pro Leu Asn Ala Tyr Ser Asp Leu Ala Glu Phe Leu Glu
1               5                   10                  15

Thr Glu Cys Tyr Gln Thr Pro Phe Asn Lys
            20                  25
```

<210> SEQ ID NO 15
<211> LENGTH: 16
<212> TYPE: PRT
<213> ORGANISM: Homo sapiens

<400> SEQUENCE: 15

```
Trp Leu Ser Asp Glu Cys Thr Asn Ala Val Val Asn Phe Leu Ser Arg
1               5                   10                  15
```

<210> SEQ ID NO 16
<211> LENGTH: 16
<212> TYPE: PRT
<213> ORGANISM: Homo sapiens

<400> SEQUENCE: 16

```
Ile Ala Val Tyr Ser Cys Pro Phe Asp Gly Met Ile Thr Glu Thr Lys
1               5                   10                  15
```

<210> SEQ ID NO 17
<211> LENGTH: 26
<212> TYPE: PRT
<213> ORGANISM: Homo sapiens

<400> SEQUENCE: 17

```
Leu Glu Val Asp Ala Ile Val Asn Ala Ala Asn Ser Ser Leu Leu Gly
1               5                   10                  15

Gly Gly Gly Val Asp Gly Cys Ile His Arg
            20                  25
```

<210> SEQ ID NO 18
<211> LENGTH: 16
<212> TYPE: PRT
<213> ORGANISM: Homo sapiens

<400> SEQUENCE: 18

```
Met Cys Asp Phe Gly Ile Ser Gly Tyr Leu Val Asp Ser Val Ala Lys
1               5                   10                  15
```

<210> SEQ ID NO 19
<211> LENGTH: 12
<212> TYPE: PRT
<213> ORGANISM: Homo sapiens

<400> SEQUENCE: 19

Leu Leu Gln Cys Asp Pro Ser Ser Ala Ser Gln Phe
1 5 10

<210> SEQ ID NO 20
<211> LENGTH: 8
<212> TYPE: PRT
<213> ORGANISM: Homo sapiens

<400> SEQUENCE: 20

Cys Glu Ser Ala Phe Leu Ser Lys
1 5

<210> SEQ ID NO 21
<211> LENGTH: 10
<212> TYPE: PRT
<213> ORGANISM: Homo sapiens

<400> SEQUENCE: 21

Ser Glu Gly Gly Phe Ile Trp Ala Cys Lys
1 5 10

<210> SEQ ID NO 22
<211> LENGTH: 11
<212> TYPE: PRT
<213> ORGANISM: Homo sapiens

<400> SEQUENCE: 22

Cys Asn Tyr Leu Ala Leu Val Gly Gly Gly Lys
1 5 10

<210> SEQ ID NO 23
<211> LENGTH: 10
<212> TYPE: PRT
<213> ORGANISM: Homo sapiens

<400> SEQUENCE: 23

Leu Leu Ser Asn Met Met Cys Gln Tyr Arg
1 5 10

<210> SEQ ID NO 24
<211> LENGTH: 12
<212> TYPE: PRT
<213> ORGANISM: Homo sapiens

<400> SEQUENCE: 24

Cys Asp Ser Ser Pro Asp Ser Ala Glu Asp Val Arg
1 5 10

<210> SEQ ID NO 25
<211> LENGTH: 53
<212> TYPE: PRT
<213> ORGANISM: Homo sapiens

<400> SEQUENCE: 25

Val Gly Ser Phe Gly Ser Ser Pro Pro Gly Leu Ser Ser Thr Tyr Thr
1 5 10 15

Gly Gly Pro Leu Gly Asn Glu Ile Ala Ser Gly Asn Gly Gly Ala Ala
20 25 30

Ala Gly Asp Asp Glu Asp Gly Gln Asn Leu Trp Ser Cys Ile Leu Ser
35 40 45

Glu Val Ser Thr Arg
50

<210> SEQ ID NO 26
<211> LENGTH: 20
<212> TYPE: PRT
<213> ORGANISM: Homo sapiens

<400> SEQUENCE: 26

```
Ile Ser Leu Gly Leu Pro Val Gly Ala Val Ile Asn Cys Ala Asp Asn
1               5                   10                  15

Thr Gly Ala Lys
            20
```

<210> SEQ ID NO 27
<211> LENGTH: 17
<212> TYPE: PRT
<213> ORGANISM: Homo sapiens

<400> SEQUENCE: 27

```
Leu Gln Phe Phe Glu Asn Cys Gly Gly Gly Ser Phe Gly Ser Val Tyr
1               5                   10                  15

Arg
```

<210> SEQ ID NO 28
<211> LENGTH: 17
<212> TYPE: PRT
<213> ORGANISM: Homo sapiens

<400> SEQUENCE: 28

```
Trp Leu Lys Gly Gln Gln Ile Gly Leu Gly Ala Phe Ser Ser Cys Tyr
1               5                   10                  15

Gln
```

<210> SEQ ID NO 29
<211> LENGTH: 16
<212> TYPE: PRT
<213> ORGANISM: Homo sapiens

<400> SEQUENCE: 29

```
Arg Leu Gly Lys Leu Leu Gly Gln Gly Ala Phe Gly Arg Val Tyr Leu
1               5                   10                  15
```

<210> SEQ ID NO 30
<211> LENGTH: 17
<212> TYPE: PRT
<213> ORGANISM: Homo sapiens

<400> SEQUENCE: 30

```
Trp Arg Arg Gly Lys Leu Leu Gly Gln Gly Ala Phe Gly Arg Val Tyr
1               5                   10                  15

Leu
```

<210> SEQ ID NO 31
<211> LENGTH: 17
<212> TYPE: PRT
<213> ORGANISM: Homo sapiens

<400> SEQUENCE: 31

```
Trp Gln Arg Gly Asn Lys Ile Gly Glu Gly Gln Tyr Gly Lys Val Tyr
1               5                   10                  15

Thr
```

-continued

<210> SEQ ID NO 32
<211> LENGTH: 17
<212> TYPE: PRT
<213> ORGANISM: Homo sapiens

<400> SEQUENCE: 32

Asn Gly Asp Arg Val Val Leu Gly Lys Gly Thr Tyr Gly Ile Val Tyr
1               5                   10                  15

Ala

<210> SEQ ID NO 33
<211> LENGTH: 17
<212> TYPE: PRT
<213> ORGANISM: Homo sapiens

<400> SEQUENCE: 33

Thr Gly Glu Arg Leu Val Leu Gly Lys Gly Thr Tyr Gly Val Val Tyr
1               5                   10                  15

Ala

<210> SEQ ID NO 34
<211> LENGTH: 17
<212> TYPE: PRT
<213> ORGANISM: Homo sapiens

<400> SEQUENCE: 34

Ile Glu Val Glu Glu Val Val Gly Arg Gly Ala Phe Gly Val Val Cys
1               5                   10                  15

Lys

<210> SEQ ID NO 35
<211> LENGTH: 17
<212> TYPE: PRT
<213> ORGANISM: Homo sapiens

<400> SEQUENCE: 35

Asn Ile Gly Ser Asp Phe Ile Pro Arg Gly Ala Phe Gly Lys Val Tyr
1               5                   10                  15

Leu

<210> SEQ ID NO 36
<211> LENGTH: 17
<212> TYPE: PRT
<213> ORGANISM: Homo sapiens

<400> SEQUENCE: 36

Leu Thr Leu Glu Glu Ile Ile Gly Ile Gly Gly Phe Gly Lys Val Tyr
1               5                   10                  15

Arg

<210> SEQ ID NO 37
<211> LENGTH: 17
<212> TYPE: PRT
<213> ORGANISM: Homo sapiens

<400> SEQUENCE: 37

Leu Gln Leu Glu Glu Ile Ile Gly Val Gly Gly Phe Gly Lys Val Tyr
1               5                   10                  15

Arg

<210> SEQ ID NO 38
<211> LENGTH: 17
<212> TYPE: PRT
<213> ORGANISM: Homo sapiens

<400> SEQUENCE: 38

Leu Arg Leu Glu Glu Val Ile Gly Ile Gly Gly Phe Gly Lys Val Tyr
1 5 10 15

Arg

<210> SEQ ID NO 39
<211> LENGTH: 17
<212> TYPE: PRT
<213> ORGANISM: Homo sapiens

<400> SEQUENCE: 39

Ile Leu Asp Leu Gln Trp Val Gly Ser Gly Ala Gln Gly Ala Val Phe
1 5 10 15

Leu

<210> SEQ ID NO 40
<211> LENGTH: 17
<212> TYPE: PRT
<213> ORGANISM: Homo sapiens

<400> SEQUENCE: 40

Ile Ser Glu Leu Gln Trp Leu Gly Ser Gly Ala Gln Gly Ala Val Phe
1 5 10 15

Leu

<210> SEQ ID NO 41
<211> LENGTH: 17
<212> TYPE: PRT
<213> ORGANISM: Homo sapiens

<400> SEQUENCE: 41

Ala Thr His Gln Leu Arg Leu Gly Arg Gly Ser Phe Gly Glu Val His
1 5 10 15

Arg

<210> SEQ ID NO 42
<211> LENGTH: 17
<212> TYPE: PRT
<213> ORGANISM: Homo sapiens

<400> SEQUENCE: 42

Asn Gly Glu Arg Val Val Leu Gly Lys Gly Thr Tyr Gly Ile Val Tyr
1 5 10 15

Ala

<210> SEQ ID NO 43
<211> LENGTH: 17
<212> TYPE: PRT
<213> ORGANISM: Homo sapiens

<400> SEQUENCE: 43

Phe Thr Asp Leu Arg Glu Ile Gly His Gly Ser Phe Gly Ala Val Tyr
1 5 10 15

Phe

-continued

```
<210> SEQ ID NO 44
<211> LENGTH: 17
<212> TYPE: PRT
<213> ORGANISM: Homo sapiens

<400> SEQUENCE: 44

Phe Ser Asp Leu Arg Glu Ile Gly His Gly Ser Phe Gly Ala Val Tyr
1               5                   10                  15

Phe


<210> SEQ ID NO 45
<211> LENGTH: 17
<212> TYPE: PRT
<213> ORGANISM: Homo sapiens

<400> SEQUENCE: 45

Phe Ile Gly Leu His Glu Ile Gly His Gly Ser Phe Gly Ala Val Tyr
1               5                   10                  15

Phe


<210> SEQ ID NO 46
<211> LENGTH: 17
<212> TYPE: PRT
<213> ORGANISM: Homo sapiens

<400> SEQUENCE: 46

Leu Glu Leu Lys Glu Leu Ile Gly Ala Gly Gly Phe Gly Gln Val Tyr
1               5                   10                  15

Arg
```